(12) United States Patent
Yoshioka et al.

(10) Patent No.: US 11,127,869 B2
(45) Date of Patent: Sep. 21, 2021

(54) PHOTOELECTRIC CONVERSION ELEMENT, OPTICAL SENSOR, IMAGING ELEMENT, AND COMPOUND

(71) Applicant: FUJIFILM Corporation, Tokyo (JP)

(72) Inventors: Tomoaki Yoshioka, Kanagawa (JP); Eiji Fukuzaki, Kanagawa (JP); Kimiatsu Nomura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 15 days.

(21) Appl. No.: 16/726,258

(22) Filed: Dec. 24, 2019

(65) Prior Publication Data
US 2020/0135951 A1 Apr. 30, 2020

Related U.S. Application Data

(63) Continuation of application No. PCT/JP2018/025078, filed on Jul. 2, 2018.

(30) Foreign Application Priority Data

Jul. 7, 2017 (JP) .............................. JP2017-133896

(51) Int. Cl.
*H01L 31/00* (2006.01)
*H01L 31/0445* (2014.01)
(Continued)

(52) U.S. Cl.
CPC .... *H01L 31/0445* (2014.12); *H01L 27/14665* (2013.01); *H01L 27/307* (2013.01);
(Continued)

(58) Field of Classification Search
CPC .................................................. H01L 51/0036
See application file for complete search history.

(56) References Cited

U.S. PATENT DOCUMENTS 8,525,577 B2 9/2013 Yofu et al.
9,070,887 B2 6/2015 Yofu et al.
(Continued)

FOREIGN PATENT DOCUMENTS

JP 2005129430 5/2005
JP 2005209359 8/2005
(Continued)

OTHER PUBLICATIONS

English machine translation of JP2014080417 (Year: 2021).*
(Continued)

*Primary Examiner* — Angelo Trivisonno
(74) *Attorney, Agent, or Firm* — JCIPRNET

(57) ABSTRACT

The invention provides a photoelectric conversion element including a photoelectric conversion film excellent in vapor deposition suitability and exhibiting excellent photoelectric conversion efficiency in a case where the photoelectric conversion film is a thin film, an optical sensor, an imaging element, and a compound. The photoelectric conversion element of the embodiment of the invention includes a conductive film, a photoelectric conversion film, and a transparent conductive film, in this order, in which the photoelectric conversion film contains a compound represented by Formula (1).

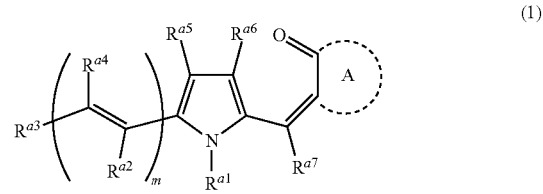

(1)

20 Claims, 7 Drawing Sheets

(51) Int. Cl.
    *H01L 27/146*     (2006.01)
    *H01L 27/30*     (2006.01)
    *H01L 51/00*     (2006.01)
    *H01L 51/42*     (2006.01)
    *H01L 51/44*     (2006.01)

(52) U.S. Cl.
    CPC ...... *H01L 51/0036* (2013.01); *H01L 51/0045* (2013.01); *H01L 51/424* (2013.01); *H01L 51/442* (2013.01)

(56) References Cited

U.S. PATENT DOCUMENTS

| | | |
|---|---|---|
| 9,941,477 B2 | 4/2018 | Choi et al. |
| 2011/0074491 A1 | 3/2011 | Yofu et al. |
| 2014/0097416 A1 | 4/2014 | Lee et al. |
| 2017/0035281 A1 | 2/2017 | Takeuchi et al. |

FOREIGN PATENT DOCUMENTS

| | | | |
|---|---|---|---|
| JP | 2011077198 | | 4/2011 |
| JP | 2014080417 A | * | 5/2014 |
| JP | 2014209610 | | 11/2014 |
| JP | 2017095460 | | 6/2017 |

OTHER PUBLICATIONS

Salman A. Khan et al., "Microwave Assisted Synthesis, Physicochemical, Photophysical, Single Crystal X-ray and DFT Studies of Novel Push-Pull Chromophores", Journal of Fluorescence, vol. 25, No. 6, Sep. 8, 2015, pp. 1585-1593.

Rosa M. F. Batista et al., "Synthesis and characterization of novel push-pull thiophene and thienylpyrrole derivatives functionalized with indanonedicyanovinyl acceptor moiety as efficient NLO-chromophores", International Conference on Applications of Optics and Photonics, May 21, 2011, pp. 1-8.

"Search Report of Europe Counterpart Application", dated May 18, 2020, p. 1-p.9.

Sakaibara, H. et al., "Reactions of 2, 3-dimethylindole and tetrahydrocarbazole with N-bromosuccimide", Tetrahedron, vol. 22, Mar. 9, 1966, pp. 2475-2479.

Harsha N. Borah et al., "Stereoselective intramolecular hetero Diels-Alder reactions of 1-oxa-1,3-butadienes: synthesis of novel annelated pyrrolo[1,2-a]indoles", Tetrahedron Letters, May 9, 2005, pp. 3391-3393.

Carole J.R. Bataille et al., "Thiazolidine derivatives as potent and selective inhibitors of the PIM kinase family", Bioorganic & Medicinal Chemistry, Feb. 28, 2017, pp. 2657-2665.

"International Search Report (Form PCT/ISA/210) of PCT/JP2018/025078," dated Aug. 21, 2018, with English translation thereof, pp. 1-5.

"International Preliminary Report on Patentability (Form PCT/IPEA/409) of PCT/JP2018/025078," completed on Jun. 17, 2019, with English translation thereof, pp. 1-15.

* cited by examiner

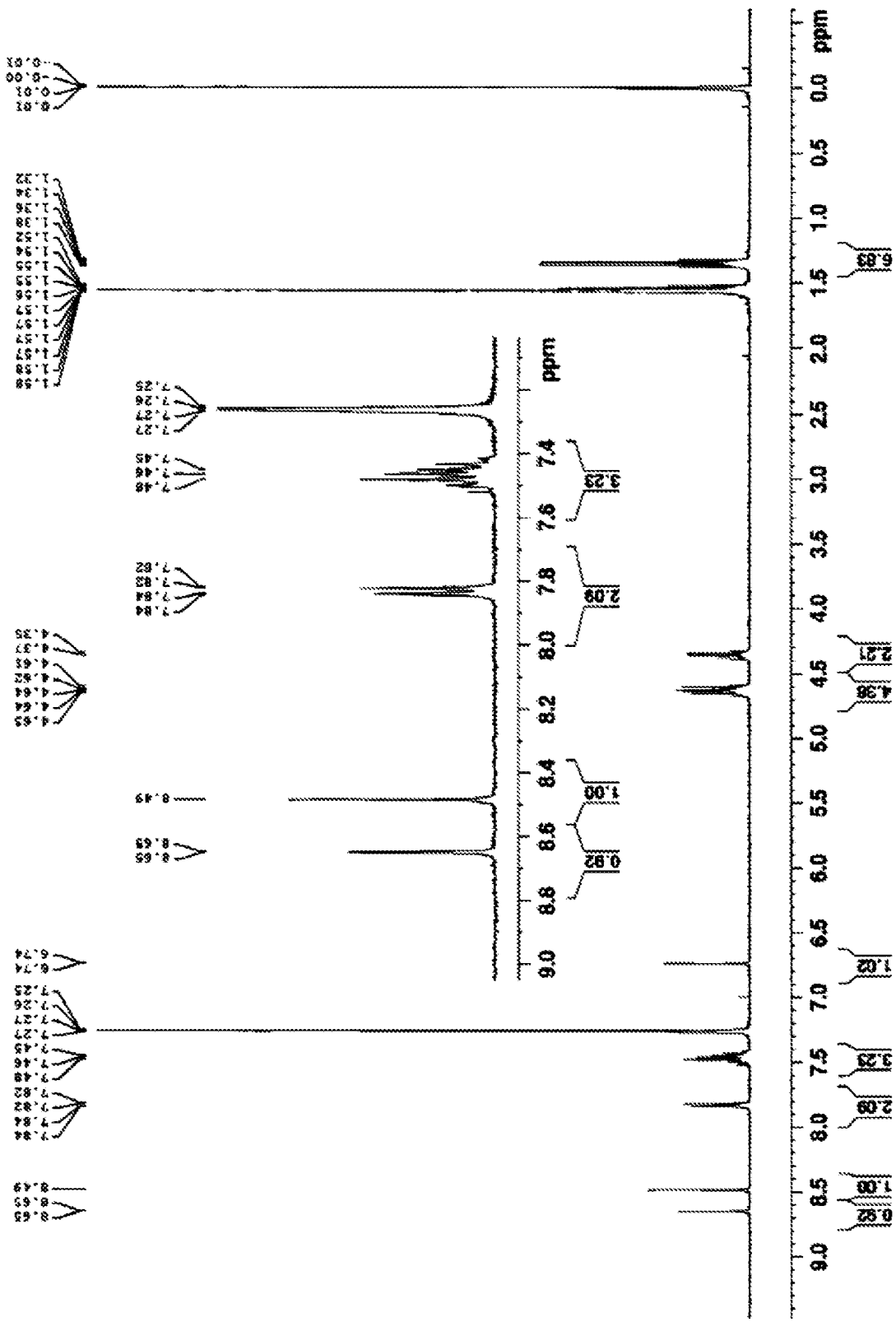

PHOTOELECTRIC CONVERSION ELEMENT, OPTICAL SENSOR, IMAGING ELEMENT, AND COMPOUND

CROSS-REFERENCE TO RELATED APPLICATIONS

This application is a Continuation of PCT International Application No. PCT/JP2018/025078 filed on Jul. 2, 2018, which claims priority under 35 U.S.C. § 119(a) to Japanese Patent Application No. 2017-133896 filed on Jul. 7, 2017. The above application is hereby expressly incorporated by reference, in its entirety, into the present application.

BACKGROUND OF THE INVENTION

1. Field of the Invention

The present invention relates to a photoelectric conversion element, an optical sensor, an imaging element, and a compound.

2. Description of the Related Art

In the related art, a planar solid-state imaging element in which photodiodes (PDs) are two-dimensionally arranged and a signal charge generated in each PD is read out by a circuit is widely used as a solid-state imaging element.

In order to realize a color solid-state imaging element, a structure in which a color filter transmitting light of a specific wavelength is disposed on a light incident surface side of the planar solid-state imaging element is generally used. Currently, a single plate solid-state imaging element in which the color filter transmitting blue (B) light, green (G) light, and red (R) light is regularly arranged on each PD which is two-dimensionally arranged is well known. However, in this single plate solid-state imaging element, light which is not transmitted through the color filter is not used, thus light utilization efficiency is poor.

In order to solve these disadvantages, in recent years, development of a photoelectric conversion element having a structure in which an organic photoelectric conversion film is disposed on a substrate for reading out a signal has progressed.

US2014/0097416A discloses, for example, a photoelectric conversion element having a photoelectric conversion film containing the following compounds.

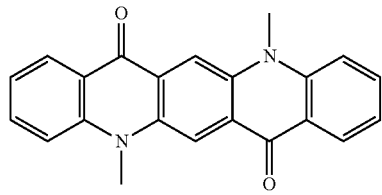 [SMILES: Cn1c2ccccc2c(=O)c2cc3c(cc21)c(=O)c1ccccc1n3C]

JP2005-209359A discloses a semiconductor for a photoelectric conversion material containing the following pigment.

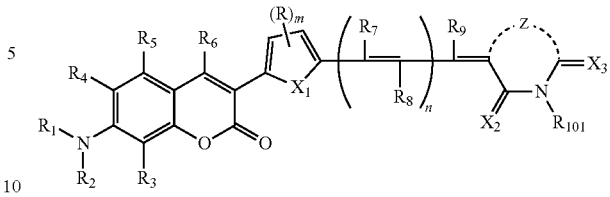

JP2005-129430A discloses a semiconductor for a photoelectric conversion material containing the following heterocyclic compound.

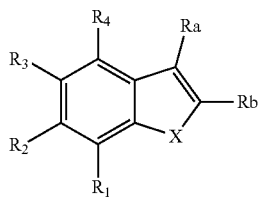

General Formula (1)

SUMMARY OF THE INVENTION

In recent years, further improvements are also required for various characteristics required for a photoelectric conversion element used in an imaging element and an optical sensor, along with demands for improving performance of the imaging element, the optical sensor, and the like.

For example, regarding the photoelectric conversion element, it is required that good photoelectric conversion efficiency can be maintained even in a case where thinning of the photoelectric conversion film is advanced (for example, in a case where the photoelectric conversion film is made to be 100 nm).

The inventors of the invention have produced a photoelectric conversion element using a compound (for example, the above-described compound) disclosed in US2014/0097416A, and have examined the photoelectric conversion efficiency in a case where the photoelectric conversion film is a thin film (hereinafter, referred to as the "photoelectric conversion efficiency in a case of a thin film"). As a result, the inventors have found that the characteristics do not necessarily reach the level required recently and further improvement is necessary.

Furthermore, the inventors of the invention have examined JP2005-209359A and JP2005-129430A and found that it is difficult to produce a photoelectric conversion film using a vapor deposition method depending on the structure of the compounds disclosed in JP2005-209359A and JP2005-129430A. Hereinafter, the suitability for producing the photoelectric conversion film when using the vapor deposition method is also referred to as "vapor deposition suitability".

In view of the above-described circumstances, an object of the invention is to provide a photoelectric conversion element including a photoelectric conversion film excellent in the vapor deposition suitability, and excellent photoelectric conversion efficiency even in a case where the photoelectric conversion film is a thin film.

Another object of the invention is to provide an optical sensor and an imaging element including the photoelectric conversion element. Still another object of the invention is to provide a compound applied to the photoelectric conversion element.

The inventors of the invention have conducted extensive studies on the above-described problems. As a result, the inventors have found that it is possible to solve the above-described problems by applying the compound having a predetermined structure to the photoelectric conversion film, and have completed the invention.

(1) A photoelectric conversion element comprising a conductive film, a photoelectric conversion film, and a transparent conductive film, in this order, in which the photoelectric conversion film contains a compound represented by Formula (1) described below.

(2) The photoelectric conversion element according to (1), in which the compound represented by Formula (1) described below is a compound represented by Formula (2) described below.

(3) The photoelectric conversion element according to (2), in which in Formula (2) described below, $R^{b1}$ represents an alkyl group, an aryl group, a heteroaryl group, a —CO-alkyl group, a —CO-aryl group, or a —CO-heteroaryl group, which may have a substituent.

(4) The photoelectric conversion element according to (2) or (3), in which in Formula (2) described below, $X^1$ represents an oxygen atom, a sulfur atom, —$NR^{b6}$—, or —$CR^{b11}$=$CR^{b12}$—.

(5) The photoelectric conversion element according to any one of (2) to (4), in which in Formula (2) described below, $X^1$ represents an oxygen atom or a sulfur atom.

(6) The photoelectric conversion element according to any one of (1) to (5), in which the compound represented by Formula (1) described below is a compound represented by Formula (3) described below.

(7) The photoelectric conversion element according to (6), in which in Formula (3) described below, $R^{c3}$ represents an aryl group or a heteroaryl group, which may have a substituent.

(8) The photoelectric conversion element according to any one of (1) to (7), in which the photoelectric conversion film further contains an n-type organic semiconductor and has a bulk hetero structure formed in a state where the compound represented by Formula (1) described below and the n-type organic semiconductor are mixed.

(9) The photoelectric conversion element according to any one of (1) to (8), further comprising one or more interlayers between the conductive film and the transparent conductive film, in addition to the photoelectric conversion film.

(10) An optical sensor comprising the photoelectric conversion element according to any one of (1) to (9).

(11) An imaging element comprising the photoelectric conversion element according to any one of (1) to (9).

(12) A compound represented by Formula (2) described below.

According to the invention, it is possible to provide a photoelectric conversion element including a photoelectric conversion film excellent in the vapor deposition suitability, and excellent photoelectric conversion efficiency even in a case where the photoelectric conversion film is a thin film.

According to the invention, it is possible to provide an optical sensor and an imaging element including the photoelectric conversion element. According to the invention, it is possible to provide a compound applied to the photoelectric conversion element.

BRIEF DESCRIPTION OF THE DRAWINGS

FIG. 7 is a $^1$H nuclear magnetic resonance (NMR) chart of a compound (D-6).

DESCRIPTION OF THE PREFERRED EMBODIMENTS

Hereinafter, preferred embodiments of a photoelectric conversion element of the invention will be described.

In the present specification, a substituent for which whether it is substituted or unsubstituted is not specified may be further substituted with a substituent (for example, a substituent W described below) within the scope not impairing an intended effect. For example, the expression of "alkyl group" refers to an alkyl group with which a substituent (for example, a substituent W described below) may be substituted.

In addition, in the present specification, the numerical range represented by "to" means a range including numerical values denoted before and after "to" as a lower limit value and an upper limit value.

The bonding direction of a divalent group represented in the present specification is not particularly limited, for example, when $X^1$ in Formula (2) described below is —N=$CR^{b13}$, in a case where a position bonded to the $R^{b3}$ side is *1, a position bonded to the pyrrole ring group side is *2, $X^1$ may be *1-N=$CR^{b13}$—*2 or *1-$CR^{b13}$=N—*2.

[Photoelectric Conversion Element]

A feature of the invention compared to the related art is that a compound represented by Formula (1) described below (hereinafter also referred to as a "specific compound") is used for a photoelectric conversion film.

The inventors of the invention have thought that in the specific compound, linking of a site acting as an acceptor having a ring represented by A of Formula (1) described below and a site acting as a donor having a pyrrole ring group contributes to the excellent photoelectric conversion efficiency in a case of a thin film.

The inventors of the invention have found that the presence of a predetermined acidic group and a salt thereof tends to have a bad influence on the vapor deposition suitability of the compound. More specifically, the inventors have found that in a case where the specific compound does not have any of a carboxy group, a salt of a carboxy group, a phosphoric acid group, a salt of a phosphoric acid group, a sulfonic acid group, or a salt of a sulfonic acid group, the excellent vapor deposition suitability can be maintained in addition to the excellent photoelectric conversion efficiency in a case of the thin film.

In the present specification, a "salt" means any one of an alkali metal salt, an alkali earth metal salt, an ammonium salt, or a substituted ammonium salt.

Figure 1A:
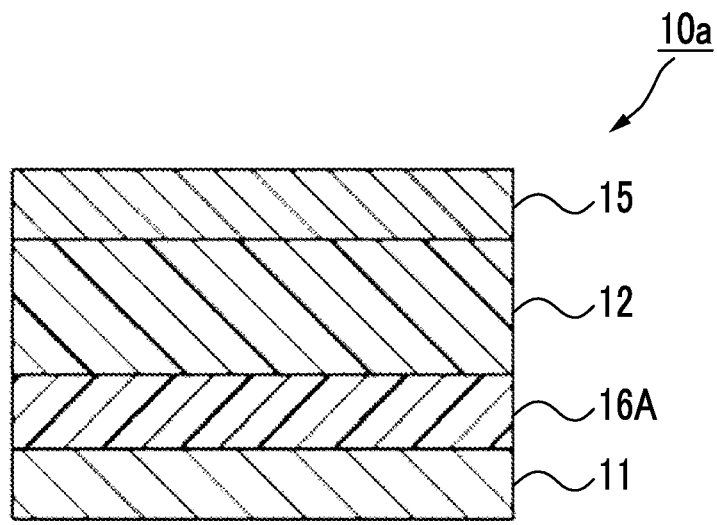
FIG. 1A is a schematic cross-sectional view showing an example of a configuration of a photoelectric conversion element.
Figure 1B:
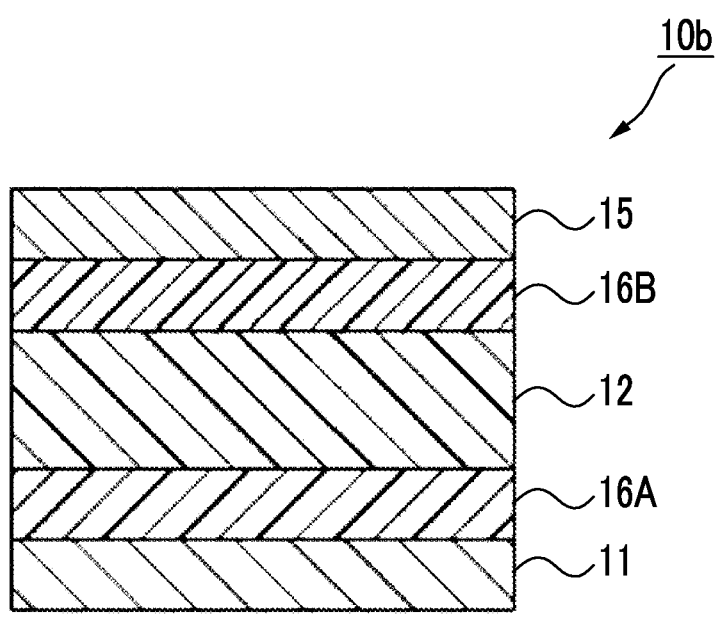
FIG. 1B is a schematic cross-sectional view showing an example of a configuration of a photoelectric conversion element.

Hereinafter, preferred embodiments of a photoelectric conversion element of the invention will be described with reference to the drawings. FIGS. 1A and 1B show schematic cross-sectional views of one embodiment of a photoelectric conversion element of the invention.

A photoelectric conversion element 10a shown in FIG. 1A has a configuration in which a conductive film (hereinafter, also referred to as a lower electrode) 11 functioning as the lower electrode, an electron blocking film 16A, a photoelectric conversion film 12 containing the specific compound described below, and a transparent conductive film (hereinafter, also referred to as an upper electrode) 15 functioning as the upper electrode are laminated in this order.

FIG. 1B shows a configuration example of another photoelectric conversion element. A photoelectric conversion element 10b shown in FIG. 1B has a configuration in which the electron blocking film 16A, the photoelectric conversion film 12, a positive hole blocking film 16B, and the upper electrode 15 are laminated on the lower electrode 11 in this order. The lamination order of the electron blocking film 16A, the photoelectric conversion film 12, and the positive hole blocking film 16B in FIGS. 1A and 1B may be appropriately changed according to the application and the characteristics.

In the photoelectric conversion element 10a (or 10b), it is preferable that light is incident on the photoelectric conversion film 12 through the upper electrode 15.

In a case where the photoelectric conversion element 10a (or 10b) is used, the voltage can be applied. In this case, it is preferable that the lower electrode 11 and the upper electrode 15 form a pair of electrodes and the voltage of $1 \times 10^{-5}$ to $1 \times 10^{7}$ V/cm is applied thereto. From the viewpoint of performance and power consumption, the voltage to be applied is more preferably $1 \times 10^{4}$ to $1 \times 10^{7}$ V/cm, and still more preferably $1 \times 10^{-3}$ to $5 \times 10^{6}$ V/cm.

The voltage application method is preferable that the voltage is applied such that the electron blocking film 16A side is a cathode and the photoelectric conversion film 12 side is an anode, in FIGS. 1A and 1B. In a case where the photoelectric conversion element 10a (or 10b) is used as an optical sensor, or also in a case where the photoelectric conversion element 10a (or 10b) is incorporated in an imaging element, the voltage can be applied by the same method.

As described in detail below, the photoelectric conversion element 10a (or 10b) can be suitably applied to applications of the optical sensor and the imaging element.

Figure 2:
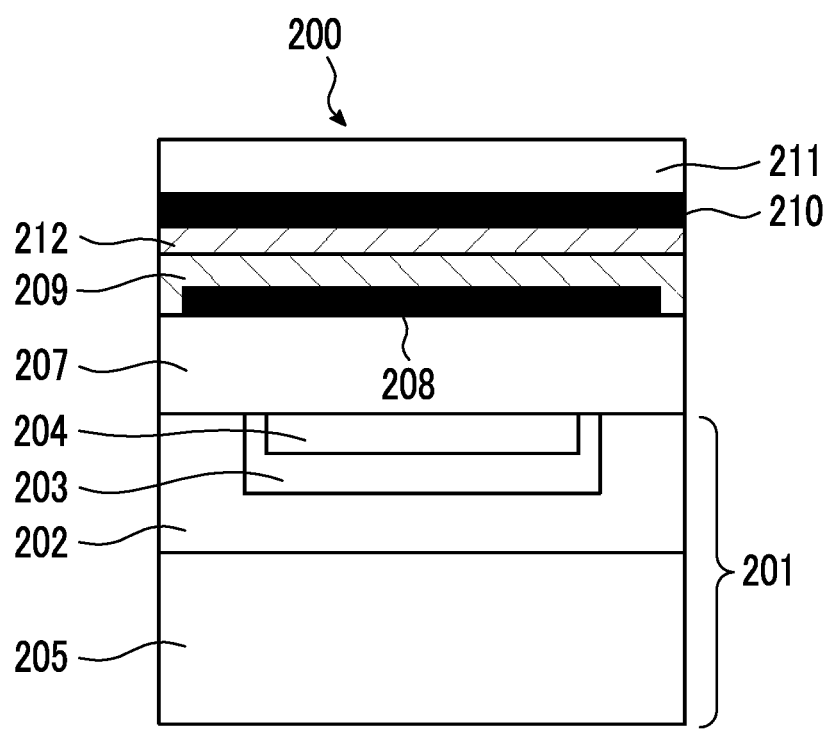
FIG. 2 is a schematic cross-sectional view of one pixel of a hybrid type photoelectric conversion element.

In addition, a schematic cross-sectional view of another embodiment of a photoelectric conversion element of the invention is shown in FIG. 2.

The photoelectric conversion element 200 shown in FIG. 2 is a hybrid type photoelectric conversion element comprising an organic photoelectric conversion film 209 and an inorganic photoelectric conversion film 201. The organic photoelectric conversion film 209 contains the specific compound described below.

The inorganic photoelectric conversion film 201 has an n-type well 202, a p-type well 203, and an n-type well 204 on a p-type silicon substrate 205.

Blue light is photoelectrically converted (a B pixel) at a p-n junction formed between the p-type well 203 and the n-type well 204, and red light is photoelectrically converted (an R pixel) at a p-n junction formed between the p-type well 203 and the n-type well 202. The conduction types of the n-type well 202, the p-type well 203, and the n-type well 204 are not limited thereto.

Furthermore, a transparent insulating layer 207 is disposed on the inorganic photoelectric conversion film 201.

A transparent pixel electrode 208 divided for each pixel is disposed on the insulating layer 207. The organic photoelectric conversion film 209 which absorbs green light and performs photoelectric conversion is disposed on the transparent pixel electrode in a single layer configuration commonly for each pixel. The electron blocking film 212 is disposed on the organic photoelectric conversion film in a single layer configuration commonly for each pixel. A transparent common electrode 210 with a single layer configuration is disposed on the electron blocking film. A transparent protective film 211 is disposed on the uppermost layer. The lamination order of the electron blocking film 212 and the organic photoelectric conversion film 209 may be reversed from that in FIG. 2, and the common electrode 210 may be disposed so as to be divided for each pixel.

The organic photoelectric conversion film 209 constitutes a G pixel for detecting green light.

The pixel electrode 208 is the same as the lower electrode 11 of the photoelectric conversion element 10a shown in FIG. 1A. The common electrode 210 is the same as the upper electrode 15 of the photoelectric conversion element 10a shown in FIG. 1A.

In a case where light from a subject is incident on the photoelectric conversion element 200, green light in the incident light is absorbed by the organic photoelectric conversion film 209 to generate optical charges. The optical charges flow into and accumulate in a green signal charge accumulation region not shown in the drawing from the pixel electrode 208.

Mixed light of the blue light and the red light transmitted through the organic photoelectric conversion film 209 enters the inorganic photoelectric conversion film 201. The blue light having a short wavelength is photoelectrically converted mainly at a shallow portion (in the vicinity of the p-n junction formed between the p-type well 203 and the n-type well 204) of a semiconductor substrate (the inorganic photoelectric conversion film) 201 to generate optical charges, and a signal is output to the outside. The red light having a long wavelength is photoelectrically converted mainly at a deep portion (in the vicinity of the p-n junction formed between the p-type well 203 and the n-type well 202) of the semiconductor substrate (the inorganic photoelectric conversion film) 201 to generate optical charges, and a signal is output to the outside.

In a case where the photoelectric conversion element 200 is used in the imaging element, a signal readout circuit (an electric charge transfer path in a case of a charge coupled device (CCD) type, or a metal-oxide-semiconductor (MOS) transistor circuit in a case of a complementary metal oxide semiconductor (CMOS) type), or the green signal charge accumulation region is formed in a surface portion of the p-type silicon substrate 205. In addition, the pixel electrode 208 is connected to the corresponding green signal charge accumulation region through vertical wiring.

Hereinafter, the form of each layer constituting the photoelectric conversion element of the embodiment of the invention will be described in detail.

[Photoelectric Conversion Film]

<Specific Compound>

The photoelectric conversion film 12 (or the organic photoelectric conversion film 209) is a film containing the specific compound as a photoelectric conversion material.

The photoelectric conversion element having the photoelectric conversion film excellent in the vapor deposition suitability and exhibiting the excellent photoelectric conversion efficiency in a case of a thin film can be obtained by using the compound.

Hereinafter, the specific compound will be described in detail.

The suitable conditions of the specific compound mentioned below are mentioned from the point which the photoelectric conversion efficiency in a case of a thin film is more excellent unless otherwise noted.

Also, unless otherwise noted, it is preferable that the substituents that may be included in the specific compound are each independently any one of the substituents W described below.

In the present specification, Formula (1) includes all geometric isomers that can be distinguished based on the C=C double bond constituted by a carbon atom to which $R^{a7}$ bonds and a carbon atom adjacent thereto in Formula (1). That is, both the cis isomer and the trans isomer which are distinguished based on the C=C double bond are included in the compound represented by Formula (1).

The same applies to geometric isomers that can be distinguished based on the C=C double bond constituted by a carbon atom to which $R^{b5}$ bonds and a carbon atom adjacent thereto in Formula (2) described below.

(Formula (1))

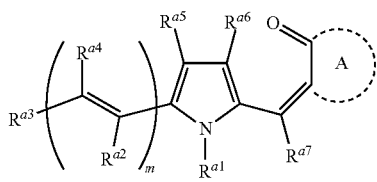

(1)

In Formula (1), m represents an integer of 0 or more. Among these, m is preferably 0 to 4, more preferably 1 to 3, and still more preferably 1.

$R^{a1}$ to $R^{a7}$ each independently represent a hydrogen atom or a substituent. The type of the substituent is not particularly limited, but a group exemplified by a substituent W described below is mentioned.

$R^{a1}$ to $R^{a7}$ may be linked to each other to form a ring.

For example, $R^{a1}$ and $R^{a2}$ may be linked to each other to form a ring, $R^{a1}$ and $R^{a7}$ may be linked to each other to form a ring, $R^{a2}$ and $R^{a3}$ may be linked to each other to form a ring, $R^{a3}$ and $R^{a4}$ may be linked to each other to form a ring, $R^{a4}$ and $R^{a5}$ may be linked to each other to form a ring, $R^{a5}$ and $R^{a6}$ may be linked to each other to form a ring, and $R^{a3}$ and $R^{a5}$ may be linked to each other to form a ring. In a case where $R^{a3}$ and $R^{a5}$ are linked to each other to form a ring, m is preferably 0. In a case where a plurality of $R^{a2}$s are present, the plurality of $R^{a2}$s may be linked to each other to form a ring.

In a case where a plurality of $R^{a4}$s are present, the plurality of $R^{a4}$s may be linked to each other to form a ring.

Among these, it is preferable that V, which is present closest to $R^{a5}$ among the plurality of $R^{a4}$s, and $R^{a5}$ are linked to each other to form a ring. In other words, it is preferable that a ring formed by bonding $R^{a4}$ and $R^{a5}$ to each other above is condensed with a pyrrole ring group specified in Formula (1) to form a condensed ring structure (a fused ring structure).

Also, the group formed by bonding $R^{a4}$ and $R^{a5}$ to each other is preferably an oxygen atom, a sulfur atom, a selenium atom, —$NR^{a8}$—, —$CR^{a9}R^{a10}$—, —$SiR^{a11}R^{a12}$—, —$CR^{a13}$=$CR^{a14}$—, —$N$=$CR^{a15}$—, or —$N$=$N$—, and more preferably an oxygen atom or a sulfur atom. $R^{a8}$ to $R^{a15}$ each independently represent a hydrogen atom or a substituent.

$R^{a1}$ which does not contribute to the formation of a ring is preferably an alkyl group, an aryl group, a heteroaryl group, a —CO-alkyl group, a —CO-aryl group, or a —CO-heteroaryl group, which may have a substituent.

$R^{a3}$ which does not contribute to the formation of a ring is preferably an alkyl group, an aryl group, a heteroaryl group, or a non-aromatic heterocyclic group, which may have a substituent, and more preferably an aryl group or a heteroaryl group.

$R^{a2}$ and $R^{a4}$ to $R^{a7}$ which do not contribute to the formation of a ring are each independently preferably a hydrogen atom, or an alkyl group, an aryl group, or a heteroaryl group, which may have a substituent.

In Formula (1), A represents a ring containing at least two carbon atoms. The two carbon atoms refer to a carbon atom in a carbonyl group in Formula (1) and a carbon atom adjacent to the carbon atom in a carbonyl group, and both the carbon atoms are atoms constituting A.

Among these, the carbon number of A is preferably 3 to 30, more preferably 3 to 20, and still more preferably 3 to 15. The above-described carbon number is a number containing two carbon atoms specified in the formula.

A may have a hetero atom. For example, the hetero atom is preferably a nitrogen atom, a sulfur atom, an oxygen atom, a selenium atom, a tellurium atom, a phosphorus atom, a silicon atom, and a boron atom, and a nitrogen atom, a sulfur atom, or an oxygen atom, and more preferably an oxygen atom.

A may have a substituent, and the substituent is preferably a halogen atom.

The number of hetero atoms in A is preferably 0 to 10, more preferably 0 to 5, and still more preferably 0 to 2. The number of hetero atoms is the number excluding the number of oxygen atoms contained in a carbonyl group constituting A specified in Formula (1) and the number of halogen atoms contained in A as a substituent.

A may or may not indicate aromaticity.

A may have a monocyclic structure or a condensed ring structure, but is preferably a 5-membered ring, a 6-membered ring, or a fused ring containing at least any one of a 5-membered ring or a 6-membered ring. The number of rings forming the fused ring is preferably 1 to 4, and more preferably 1 to 3.

Among these, it is preferable that the ring represented by A has a group represented by Formula (A1) below. In addition, *$^1$ represents the bonding position with the carbon atom in the carbonyl group constituting A specified in Formula (1), and *$^2$ represents the bonding position with the other carbon atom different from the carbon atom in the carbonyl group constituting A specified in Formula (1).

*$^1$-L-Y—Z—*$^2$ (A1)

In Formula (A1), L represents a single bond or —$NR^L$—.

$R^L$ represents a hydrogen atom or a substituent. Among these, $R^L$ is preferably an alkyl group, an aryl group, or a heteroaryl group, and more preferably an alkyl group or an aryl group.

L is preferably a single bond.

Y represents —CR$^{Y1}$=CR$^{Y2}$—, —CS—NR$^{Y3}$—, —CS—, —NR$^{Y4}$—, or —N=CR$^{Y5}$—, and among these, —CR$^{Y1}$=CR$^{Y2}$— is preferable.

R$^{Y1}$ to R$^{Y5}$ each independently represent a hydrogen atom or a substituent. Among these, R$^{Y1}$ to R$^{Y5}$ are each independently preferably an alkyl group, an aryl group, or a heteroaryl group, and more preferably an alkyl group or an aryl group.

In a case where Y represents —CR$^{Y1}$=CR$^{Y2}$—, it is preferable that R$^{Y1}$ and R$^{Y2}$ are linked to each other to form a ring, and more preferable that R$^{Y1}$ and R$^{Y2}$ are linked to each other to form a benzene ring.

Z represents a single bond, —CO—, or —S—, and among these, —CO— is preferable.

The above-described combination of L, Y, and Z is preferably a combination in which a ring formed by bonding -L-Y—Z— and two carbon atoms specified in Formula (1) to each other is a 5-membered ring or a 6-membered ring. However, the 5-membered ring or the 6-membered ring may be further condensed with a different ring (preferably, a benzene ring) to form a condensed ring structure as described above.

Among these, the group represented by Formula (A1) is more preferably a group represented by Formula (A2) below.

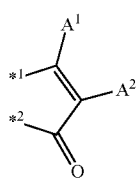

(A2)

In Formula (A2), A$^1$ and A$^2$ each independently represent a hydrogen atom or a substituent.

It is preferable that A$^1$ and A$^2$ are linked to each other to form a ring, and more preferable that A$^1$ and A$^2$ are linked to each other to form a benzene ring.

The benzene ring formed by A$^1$ and A$^2$ preferably further has a substituent. Example of a substituent is preferably a halogen atom, and more preferably a chlorine atom or a fluorine atom.

Also, the substituent included in the benzene ring formed by A$^1$ and A$^2$ may be further linked to each other to form a ring. For example, the substituent included in the benzene ring formed by A$^1$ and A$^2$ may be further linked to each other to form a benzene ring.

Among these, the group represented by Formula (A1) is still more preferably a group represented by Formula (A3) below.

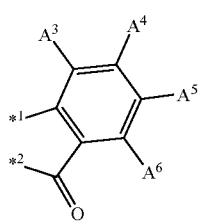

(A3)

In Formula (A3), A$^3$ to A$^6$ each independently represent a hydrogen atom or a substituent. Among these, A$^3$ to A$^6$ are each independently preferably a hydrogen atom or a halogen atom, and more preferably a hydrogen atom, a chlorine atom, or a fluorine atom.

A$^3$ and A$^4$ may be linked to each other to form a ring, A$^4$ and A$^5$ may be linked to each other to form a ring, and A$^5$ and A$^6$ may be linked to each other to form a ring. The ring formed by linking A$^3$ and A$^4$, A$^4$ and A$^5$, and A$^5$ and A$^6$ to each other is preferably a benzene ring.

Among these, it is preferable that A$^4$ and A$^5$ are linked to each other to form a ring, and the ring formed by linking A$^4$ and A$^5$ to each other is preferably a benzene ring. The ring formed by linking A$^4$ and A$^5$ to each other may be further substituted with a substituent.

Such a ring is preferably a substance normally used as an acidic nucleus with a merocyanine dye, and the specific examples thereof include the followings.

(a) 1,3-Dicarbonyl nucleus: for example, 1,3-indandione nucleus, 1,3-cyclohexanedione, 5,5-dimethyl-1,3-cyclohexanedione, 1,3-dioxane-4,6-dione, and the like.

(b) Pyrazolinone nucleus: for example, 1-phenyl-2-pyrazolin-5-one, 3-methyl-1-phenyl-2-pyrazolin-5-one, 1-(2-benzothiazolyl)-3-methyl-2-pyrazolin-5-one, and the like.

(c) Isoxazolinone nucleus: for example, 3-phenyl-2-isoxazolin-5-one, 3-methyl-2-isoxazolin-5-one, and the like.

(d) Oxindole nucleus: for example, 1-alkyl-2,3-dihydro-2-oxindole, and the like.

(e) 2,4,6-Trioxohexahydropyrimidine nucleus: for example, barbituric acid, 2-thiobarbituric acid and derivatives thereof, or the like. Examples of the derivative include a 1-alkyl form such as 1-methyl and 1-ethyl, a 1,3-dialkyl form such as 1,3-dimethyl, 1,3-diethyl, and 1,3-dibutyl, a 1,3-diaryl form such as 1,3-diphenyl, 1,3-di(p-chlorophenyl), 1,3-di(p-ethoxycarbonylphenyl), 1-alkyl-1-aryl form such as 1-ethyl-3-phenyl, and a 1,3-diheteroaryl form such as 1,3-di(2-pyridyl).

(f) 2-Thio-2,4-thiazolidinedione nucleus: for example, rhodanine and derivatives thereof. Examples of the derivatives include 3-alkylrhodanine such as 3-methylrhodanine, 3-ethylrhodanine, and 3-allylrhodanine, 3-arylrhodanine such as 3-phenylrhodanine, and 3-heteroaryl rhodanine such as 3-(2-pyridyl)rhodanine.

(g) 2-Thio-2,4-oxazolidinedione(2-thio-2,4-(3H, 5H)-oxazoledione nucleus: for example, 3-ethyl-2-thio-2,4-oxazolidinedione, and the like.

(h) Tianaphthenone nucleus: for example, 3(2H)-thianaphthenone-1,1-dioxide, and the like.

(i) 2-Thio-2,5-thiazolidinedione nucleus: for example, 3-ethyl-2-thio-2,5-thiazolidinedione, and the like.

(j) 2,4-Thiazolidinedione nucleus: for example, 2,4-thiazolidinedione, 3-ethyl-2,4-thiazolidinedione, 3-phenyl-2,4-thiazolidinedione, and the like.

(k) Thiazolin-4-one nucleus: for example, 4-thiazolinone, 2-ethyl-4-thiazolinone, and the like.

(l) 2,4-Imidazolidinedione (hydantoin) nucleus: for example, 2,4-imidazolidinedione, 3-ethyl-2,4-imidazolidinedione, and the like.

(m) 2-Thio-2,4-imidazolidinedione (2-thiohydantoin) nucleus: for example, 2-thio-2,4-imidazolidinedione, 3-ethyl-2-thio-2,4-imidazolidinedione, and the like.

(n) Imidazolin-5-one nucleus: for example, 2-propylmercapto-2-imidazolin-5-one, and the like.

(o) 3,5-Pyrazolidinedione nucleus: for example, 1,2-diphenyl-3,5-pyrazolidinedione, 1,2-dimethyl-3,5-pyrazolidinedione, and the like.

(p) Benzothiophene-3(2H)-one nucleus: for example, benzothiophene-3(2H)-one, oxobenzothiophene-3(2H)-one, dioxobenzothiophene-3(2H)-one, and the like.

(q) Indanone nucleus: for example, 1-indanone, 3-phenyl-1-indanone, 3-methyl-1-indanone, 3,3-diphenyl-1-indanone, 3,3-dimethyl-1-indanone, and the like.

(r) Benzofuran-3-(2H)-one nucleus: for example, benzofuran-3-(2H)-one, and the like.

(s) 2,2-Dihydrophenalene-1,3-dione nucleus, and the like.

The specific compound does not have any of a carboxy group, a salt of a carboxy group, a phosphoric acid group, a salt of a phosphoric acid group, a sulfonic acid group, or a salt of a sulfonic acid group from the viewpoint of avoiding deterioration in the vapor deposition suitability.

In addition to the above-described groups and the salts thereof, from the viewpoint of avoiding deterioration in the vapor deposition suitability, it is preferable that the specific compound does not have any of a sulfuric monoester group, a monophosphate group, a phosphonic acid group, a phosphinic acid group, a boric acid group, and salts thereof.

(Formula (2))

The specific compound is preferably a compound represented by Formula (2) below.

Formula (2) below corresponds to a case where m in Formula (1) represents 1 and $R^{a4}$ and $R^{a5}$ are linked to each other to form a ring.

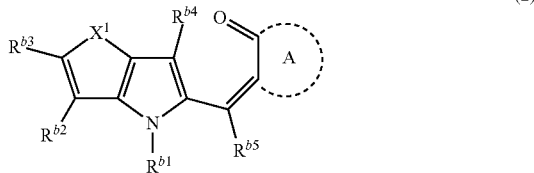

(2)

In Formula (2), $R^{b1}$ to $R^{b5}$ each independently represent a hydrogen atom or a substituent. The type of the substituent is not particularly limited, but a group exemplified by a substituent W described below is mentioned.

Among these, $R^{b1}$ is preferably an alkyl group, an aryl group, a heteroaryl group, a —CO-alkyl group, a —CO-aryl group, or a —CO-heteroaryl group, which may have a substituent, more preferably an alkyl group or an aryl group, and still more preferably an alkyl group having 1 to 2 carbon atoms, a cyclohexyl group, or a phenyl group.

It is preferable that the phenyl group has an alkyl group (preferably, a branched alkyl group having 3 to 5 carbon atoms) as a substituent.

$R^{b3}$ is preferably an alkyl group, an aryl group, a heteroaryl group, or a non-aromatic heterocyclic group (for example, a piperidine ring group), which may have a substituent, more preferably an aryl group or a heteroaryl group, which may have a substituent, and still more preferably a phenyl group, a naphthyl group, a thienyl group, or a carbazole ring group, which may have a substituent.

It is preferable that the aryl group or the heteroaryl group represented by $R^{b3}$ has, as a substituent, an alkyl group (more preferably, a linear or branched alkyl group having 1 to 5 carbon atoms), an alkoxy group (more preferably, a methoxy group), or an aryl group (more preferably, a phenyl group). It is also preferable that the alkyl group, the alkoxy group, and the aryl group as a substituent further have a substituent, and the substituent thereof is preferably a halogen atom (more preferably a fluorine atom).

$R^{b2}$, $R^{b4}$, and $R^{b5}$ are each independently preferably a hydrogen atom, or an alkyl group, an aryl group, or a heteroaryl group, which may have a substituent, and more preferably a hydrogen atom.

$X^1$ represents an oxygen atom, a sulfur atom, a selenium atom, —NR$^{b6}$—, —CR$^{b7}$R$^{b8}$—, —SiR$^{b9}$R$^{b10}$—, —CR$^{b11}$═CR$^{b12}$—, —N═CR$^{b13}$—, or —N═N—. $R^{b6}$ to $R^{b13}$ each independently represent a hydrogen atom or a substituent. $R^{b6}$ to $R^{b13}$ are each independently preferably a hydrogen atom, or an alkyl group, an aryl group (a phenyl group), a heteroaryl group, or a non-aromatic heterocyclic group (a piperidine ring group), which may have a substituent.

Among these, $X^1$ is preferably an oxygen atom, a sulfur atom, —NR$^{b6}$—, or —CR$^{b11}$═CR$^{b12}$—, and more preferably an oxygen atom or a sulfur atom.

$R^{b2}$ and $R^{b3}$ may be linked to each other to form a ring.

In a case where $X^1$ represents —NR$^{b6}$—, —CR$^{b7}$R$^{b8}$—, —SiR$^{b9}$R$^{b10}$—, —CR$^{b11}$═CR$^{b12}$—, or —N═CR$^{b13}$—, any one of $R^{b6}$, $R^{b7}$, $R^{b8}$, $R^{b9}$, $R^{b10}$, $R^{b11}$, $R^{b12}$, or $R^{b13}$ included in the group represented by $X^1$ and $R^{b3}$ may be linked to each other to form a ring.

$R^{b4}$ and $R^{b5}$ are not linked to each other to form a ring.

A in Formula (2) represents a ring containing at least two carbon atoms, and the preferred embodiment of A in Formula (2) is the same as the preferred embodiment of A in Formula (1).

As described above, the compound represented by Formula (2) does not have any of a carboxy group, a salt of a carboxy group, a phosphoric acid group, a salt of a phosphoric acid group, a sulfonic acid group, or a salt of a sulfonic acid group.

(Formula (3))

The specific compound is more preferably a compound represented by Formula (3) below.

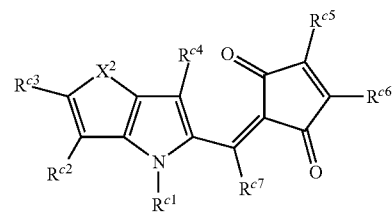

(3)

In Formula (3), $R^{c1}$ represents an alkyl group, an aryl group, a heteroaryl group, a —CO-alkyl group, a —CO-aryl group, or a —CO-heteroaryl group, which may have a substituent. Among these, an alkyl group or an aryl group is preferable, and an alkyl group having 1 to 2 carbon atoms, a cyclohexyl group, or a phenyl group is more preferable.

It is preferable that the phenyl group has an alkyl group (preferably, a branched alkyl group having 3 to 5 carbon atoms) as a substituent.

$R^{c2}$ to $R^{c7}$ each independently represent a hydrogen atom or a substituent. The type of the substituent is not particularly limited, but a group exemplified by a substituent W described below is mentioned.

$R^{c3}$ is preferably an alkyl group, an aryl group, a heteroaryl group, or a non-aromatic heterocyclic group (for example, a piperidine ring group), which may have a substituent, more preferably an aryl group or a heteroaryl group, which may have a substituent, and still more preferably a phenyl group, a naphthyl group, a thienyl group, or a carbazole ring group, which may have a substituent.

It is preferable that the aryl group or the heteroaryl group represented by $R^{c3}$ has, as a substituent, an alkyl group (more preferably, a linear or branched alkyl group having 1 to 5 carbon atoms), an alkoxy group (more preferably, a methoxy group), or an aryl group (more preferably, a phenyl group). It is also preferable that the alkyl group, the alkoxy group, and the aryl group as a substituent further have a substituent, and the substituent thereof is preferably a halogen atom (more preferably a fluorine atom).

$R^{c2}$ and $R^{c3}$ may be linked to each other to form a ring, and $R^{c5}$ and $R^{c6}$ may be linked to each other to form a ring.

Among these, it is preferable that $R^{c5}$ and $R^{c6}$ are linked to each other to form a benzene ring. That is, it is preferable to form a group corresponding to a group represented Formula (A3). In this case, the preferred embodiment of the group corresponding to the group represented by Formula (A3) above is the same as the preferred embodiment of the group represented by Formula (A3). In this case, the carbon atom to which $R^{c5}$ specified in Formula (3) bonds corresponds to the carbon atom adjacent to $*^1$ in Formula (A3).

$R^{c2}$, $R^{c4}$, and $R^{c7}$, are each independently preferably a hydrogen atom, or an alkyl group, an aryl group, or a heteroaryl group, and more preferably a hydrogen atom.

$X^2$ represents an oxygen atom or a sulfur atom.

$R^{c4}$ and $R^{c7}$ are not linked to each other to form a ring.

As described above, the compound represented by Formula (3) does not have any of a carboxy group, a salt of a carboxy group, a phosphoric acid group, a salt of a phosphoric acid group, a sulfonic acid group, or a salt of a sulfonic acid group.

(Substituent W)

The substituent W in the present specification will be described below.

Examples of the substituent W include a halogen atom, an alkyl group (including a cycloalkyl group, a bicycloalkyl group, and a tricycloalkyl group), an alkenyl group (including a cycloalkenyl group and a bicycloalkenyl group), an alkynyl group, an aryl group, a heterocyclic group, a cyano group, a hydroxy group, a nitro group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonium group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, a boronic acid group ($—B(OH)_2$), and other well-known substituents.

Also, the substituent W may be further substituted with the substituent W. For example, an alkyl group may be substituted with a halogen atom.

The details of the substituent W are disclosed in paragraph [0023] of JP2007-234651A.

However, as described above, the specific compound does not have any of a carboxy group, a salt of a carboxy group, a phosphoric acid group, a salt of a phosphoric acid group, a sulfonic acid group, or a salt of a sulfonic acid group from the viewpoint of avoiding deterioration in the vapor deposition suitability. Therefore, in the present specification, the substituent W included in the specific compound does not contain a carboxy group, a salt of a carboxy group, a phosphoric acid group, a salt of a phosphoric acid group, a sulfonic acid group, and a salt of a sulfonic acid group.

The carbon number of an alkyl group included in the specific compound (the compound represented by Formulae (1) to (3)) is not particularly limited, but preferably 1 to 10, more preferably 1 to 6, and still more preferably 1 to 4. The alkyl group may be linear, branched, or cyclic. The alkyl group may be substituted with a substituent (for example, the substituent W).

Examples of the alkyl group include a methyl group, an ethyl group, an n-propyl group, an i-propyl group, an n-butyl group, a t-butyl group, an n-hexyl group, and a cyclohexyl group.

The carbon number of an aryl group included in the specific compound (the compound represented by Formulae (1) to (3)) is not particularly limited, but preferably 6 to 30, more preferably 6 to 18, and still more preferably 6. The aryl group may have a monocyclic structure or a condensed ring structure (a fused ring structure) in which two or more rings are condensed. An aryl group may be substituted with a substituent (for example, the substituent W).

Examples of the aryl group include a phenyl group, a naphthyl group, an anthryl group, a pyrenyl group, a phenanthrenyl group, a methylphenyl group, a dimethylphenyl group, a biphenyl group, and a fluorenyl group, and a phenyl group, a naphthyl group, or an anthryl group is preferable.

The carbon number of a heteroaryl group (a monovalent aromatic heterocyclic group) included in the specific compound (the compound represented by Formulae (1) to (3)) is not particularly limited, but preferably 3 to 30, and more preferably 3 to 18. The heteroaryl group may be substituted with a substituent (for example, the substituent W).

The heteroaryl group includes a hetero atom in addition to a carbon atom and a hydrogen atom. Examples of the hetero atom include a sulfur atom, an oxygen atom, a nitrogen atom, a selenium atom, a tellurium atom, a phosphorus atom, a silicon atom, and a boron atom, and a sulfur atom, an oxygen atom, or a nitrogen atom is preferable.

The number of hetero atoms contained in the heteroaryl group is not particularly limited, but is usually about 1 to 10, preferably 1 to 4, and more preferably 1 to 2.

The number of ring members of the heteroaryl group is not particularly limited, but is preferably 3 to 8, more preferably 5 to 7, and still more preferably 5 to 6. The heteroaryl group may have a monocyclic structure or a condensed ring structure in which two or more rings are condensed. In a case of the condensed ring structure, an aromatic hydrocarbon ring having no hetero atom (for example, a benzene ring) may be included.

Examples of the heteroaryl group include a pyridyl group, a quinolyl group, an isoquinolyl group, an acridinyl group, a phenanthridinyl group, a pteridinyl group, a pyrazinyl group, a quinoxalinyl group, a pyrimidinyl group, a quinazolyl group, a pyridazinyl group, a cinnolinyl group, a phthalazinyl group, a triazinyl group, an oxazolyl group, a benzoxazolyl group, a thiazolyl group, a benzothiazolyl group, an imidazolyl group, a benzimidazolyl group, a pyrazolyl group, an indazolyl group, an isoxazolyl group, a benzisoxazolyl group, an isothiazolyl group, a benzisothiazolyl group, an oxadiazolyl group, a thiadiazolyl group, a triazolyl group, a tetrazolyl group, a furyl group, a benzofuryl group, a thienyl group, a benzothienyl group, a dibenzofuryl group, a dibenzothienyl group, a pyrrolyl group, an indolyl group, an imidazopyridinyl group, and a carbazolyl group.

Hereinafter, the compound represented by Formula (1) will be exemplified.

In a case where the compound was applied to Formula (1) (or Formula (2)), the structural formula shown below intends to include both the cis isomer and the trans isomer which are distinguished based on a group corresponding to the C=C double bond constituted by a carbon atom to which $R^{a7}$ (or $R^{b5}$) bonds and a carbon atom adjacent thereto.

In the following examples, "Me" represents a methyl group and "TMS" represents a trimethylsilyl group.

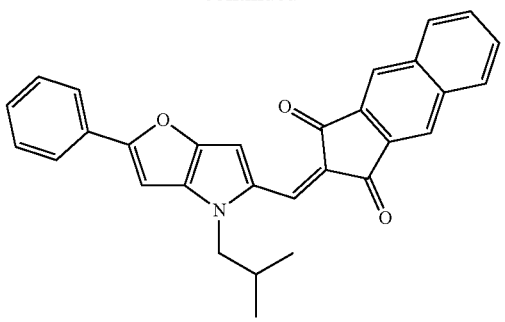

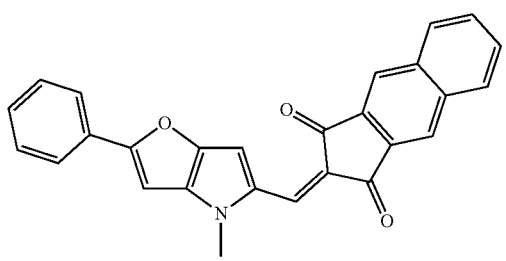

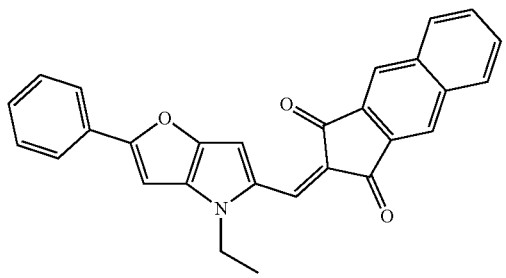

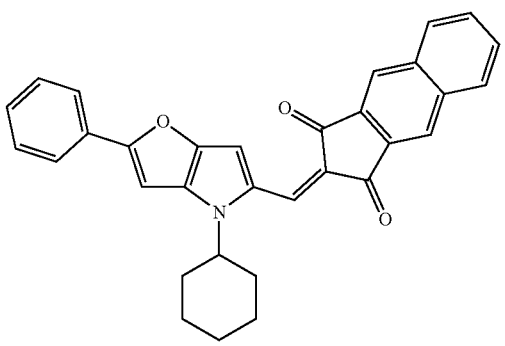

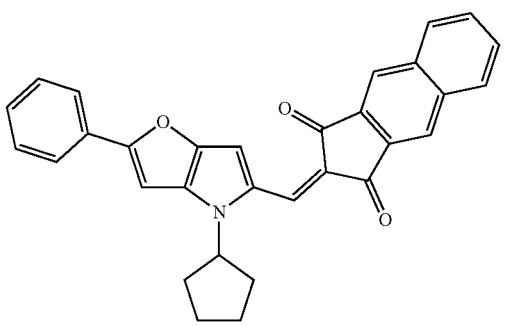

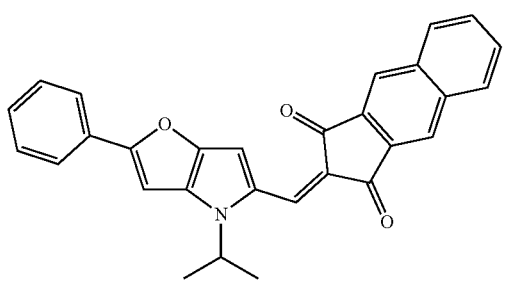

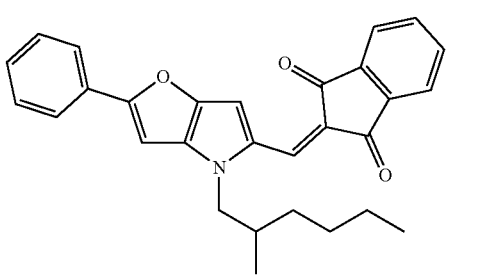

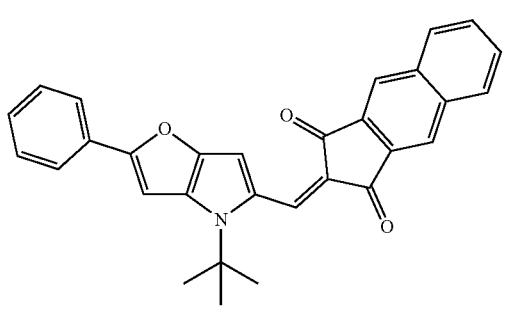

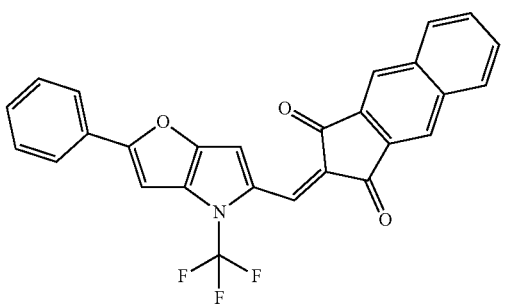

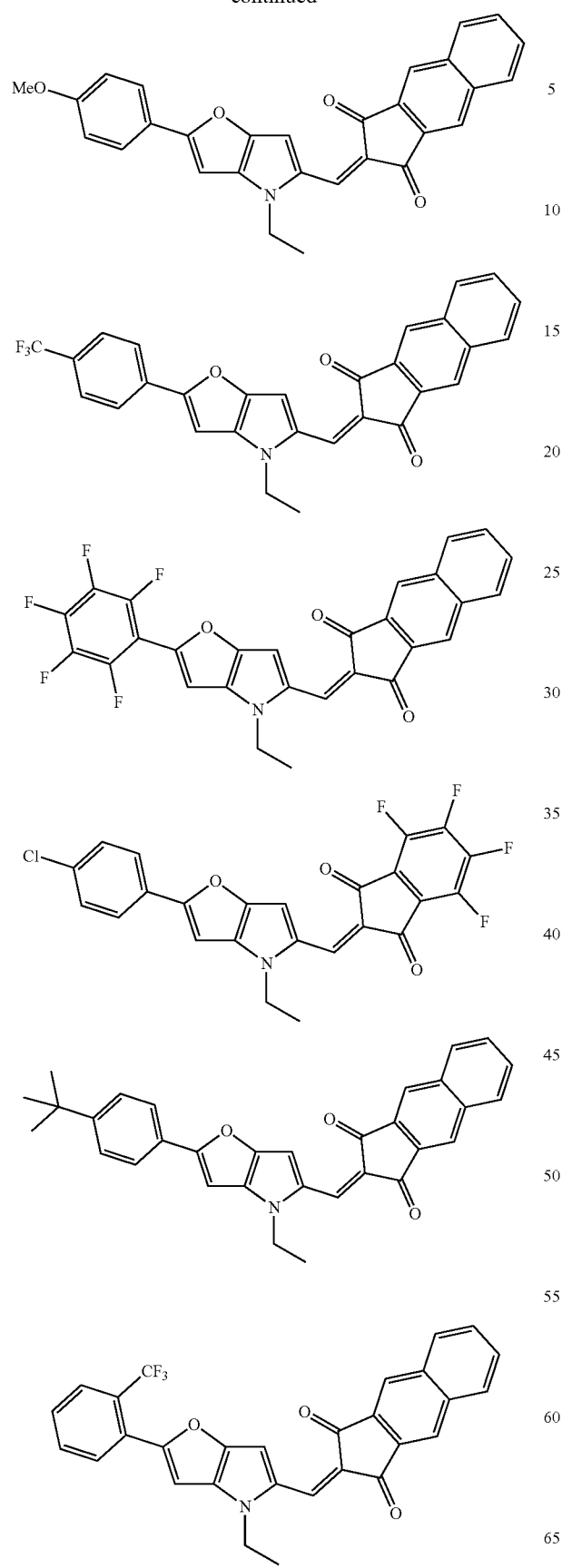

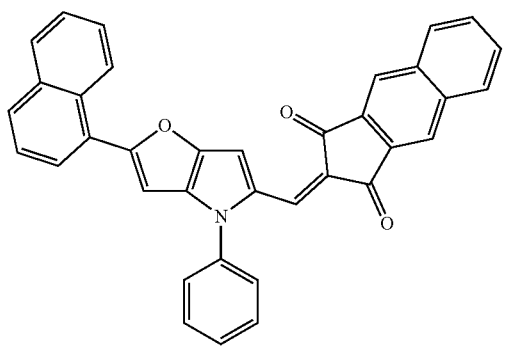
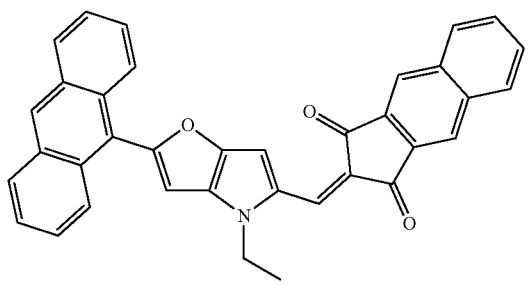
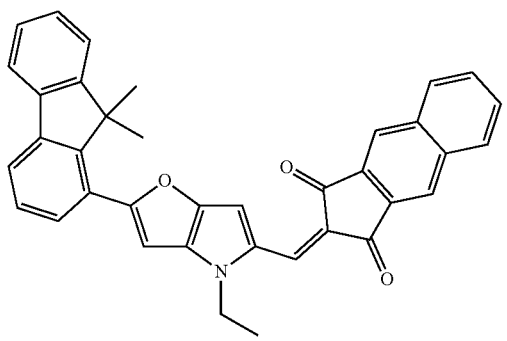
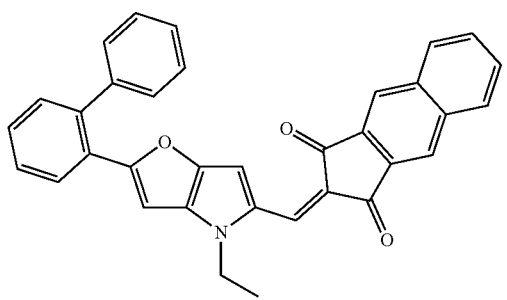
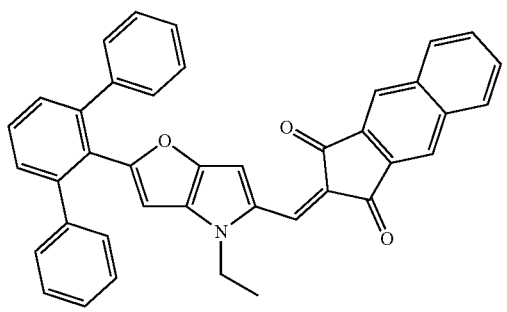
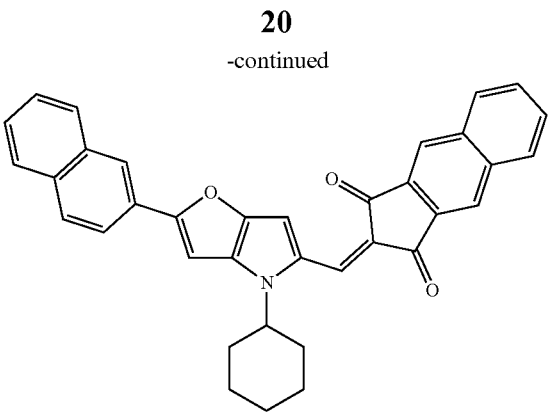
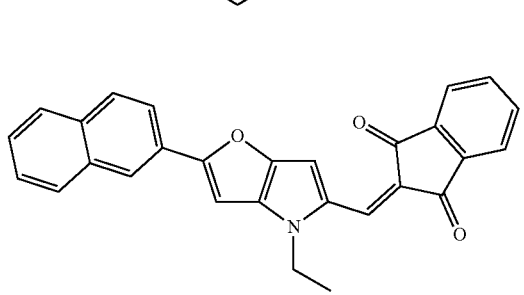
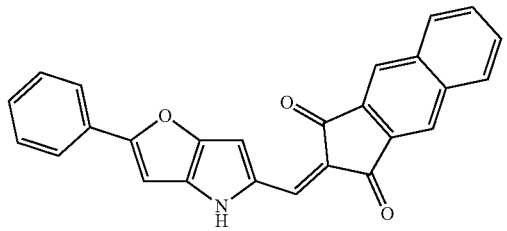
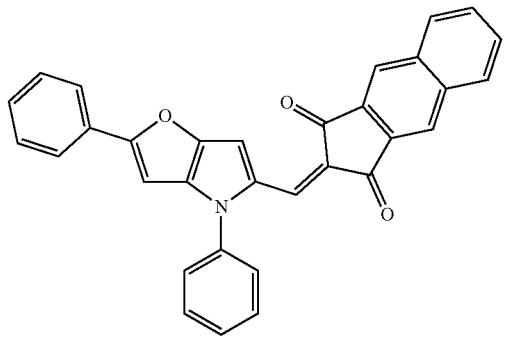
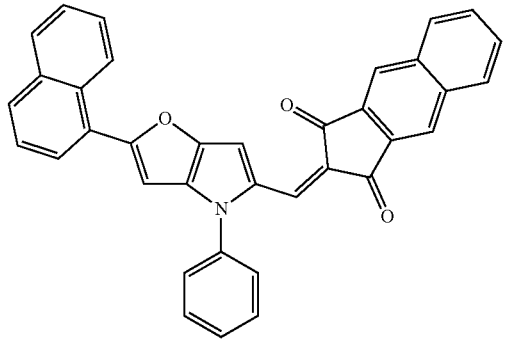

21
-continued
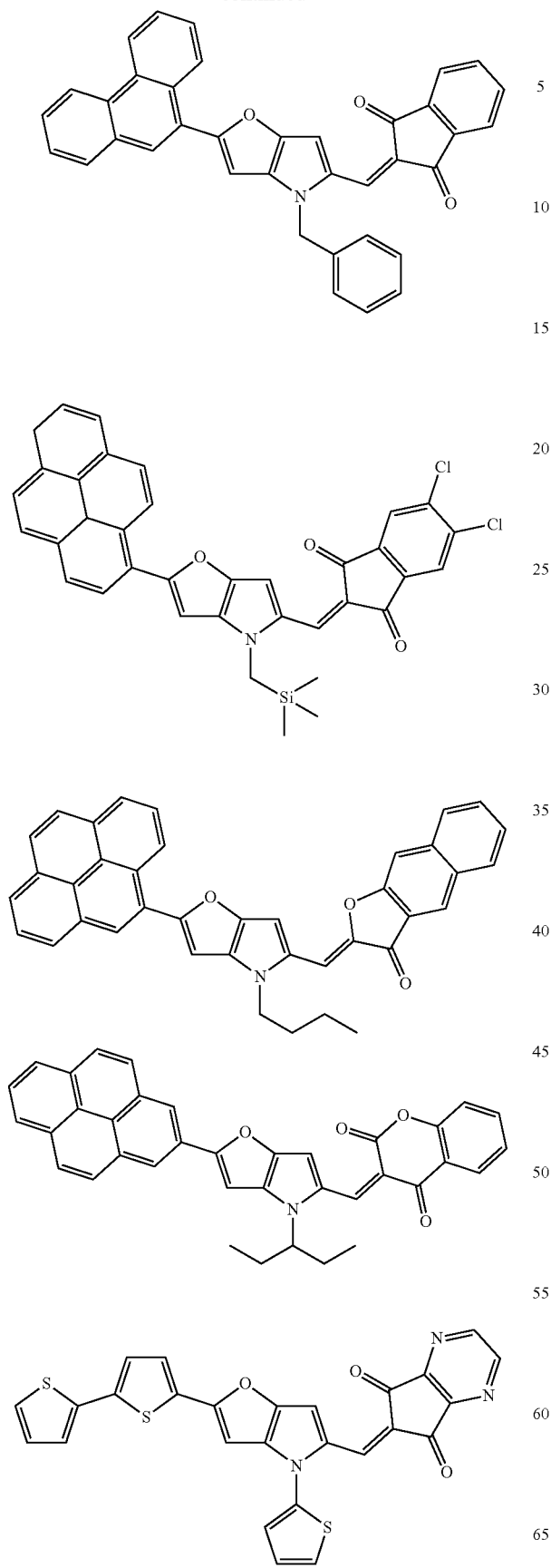
22
-continued
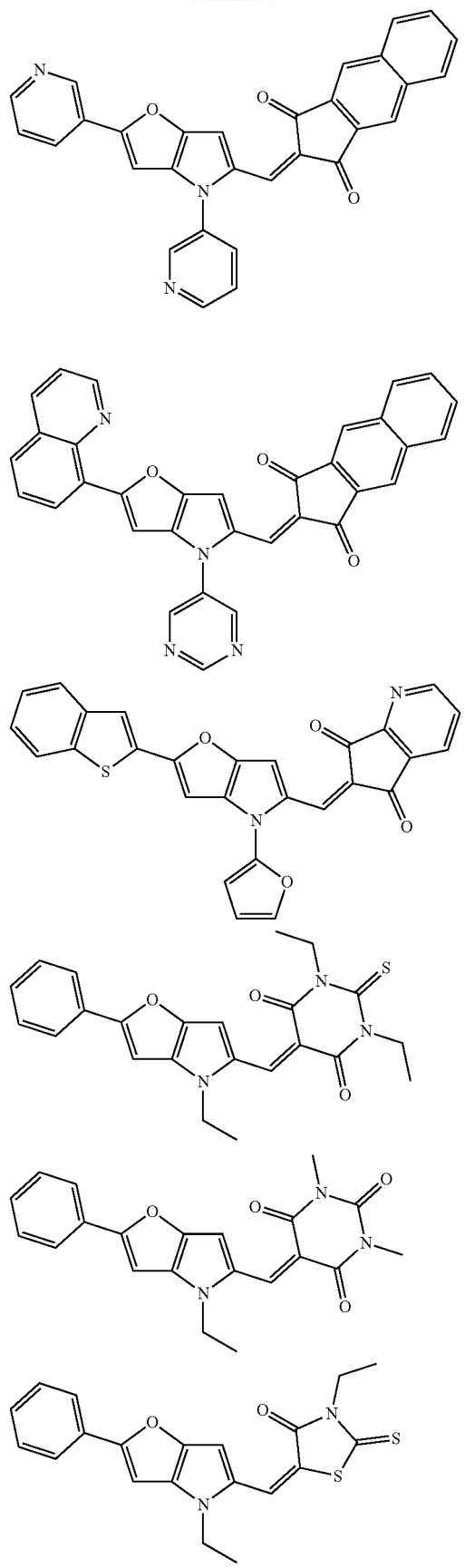

23
-continued
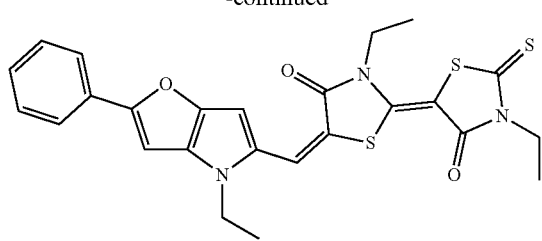
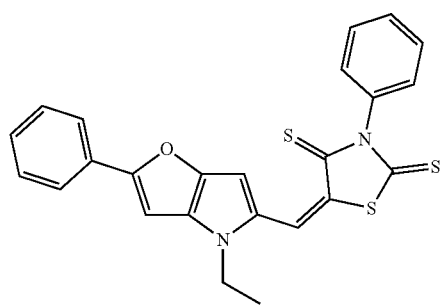
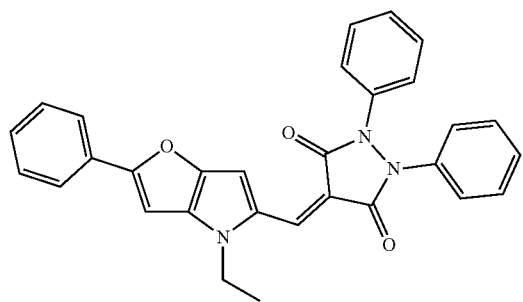
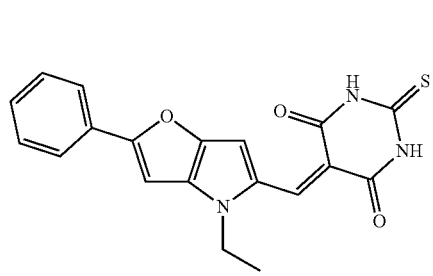
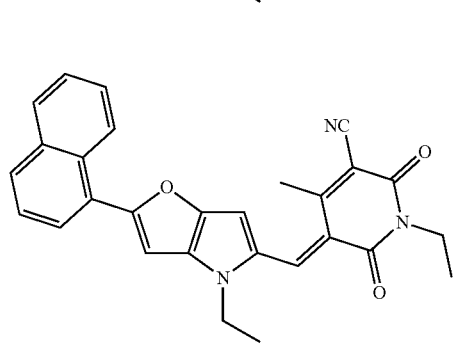
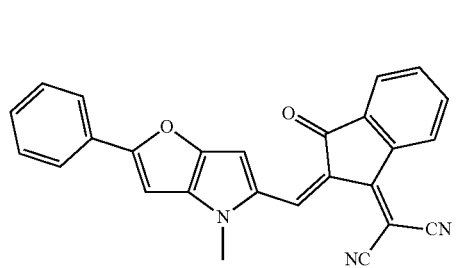
24
-continued
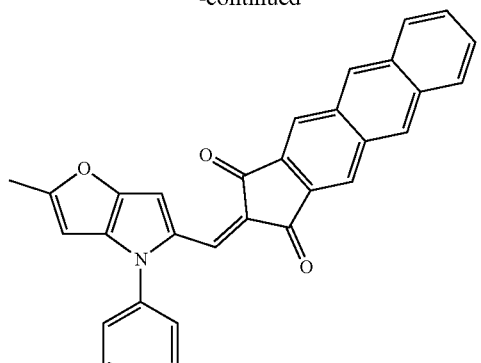
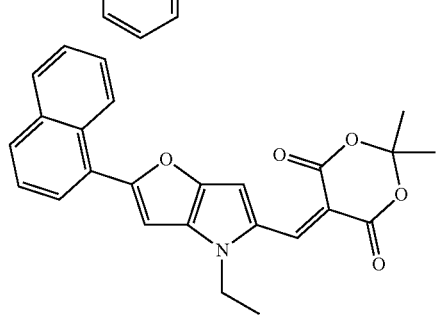
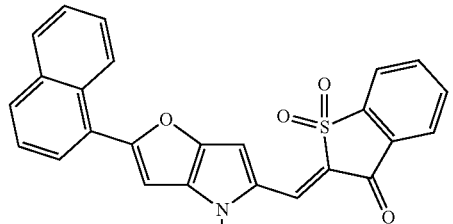
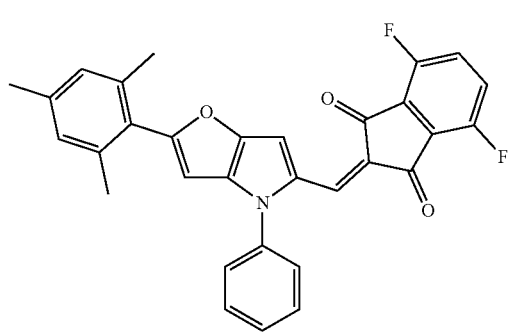
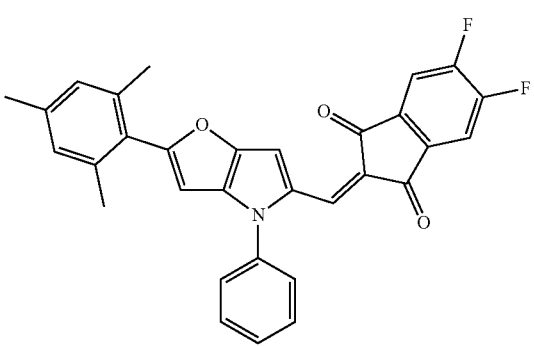

-continued
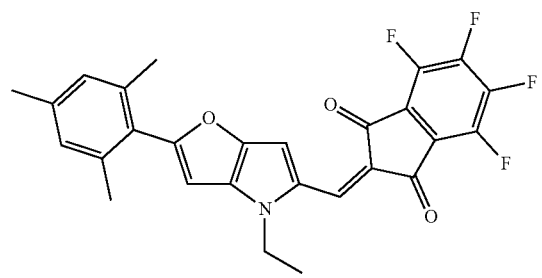
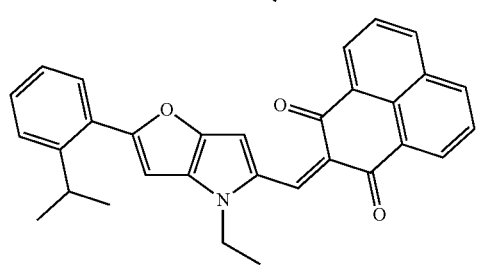
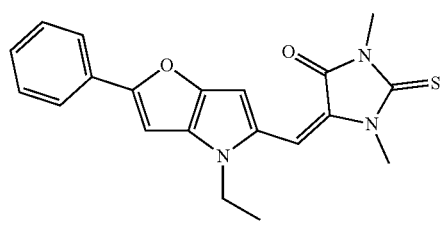
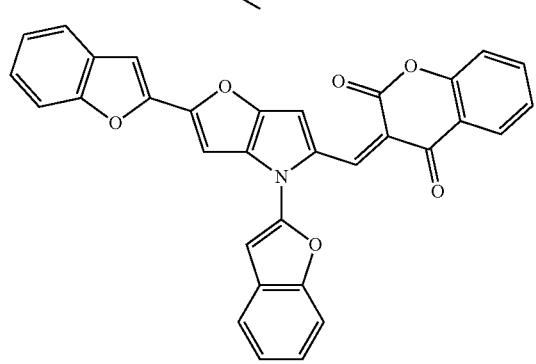
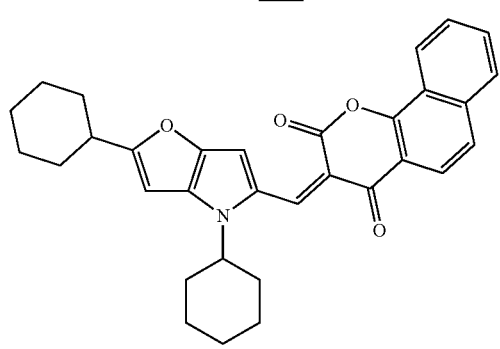
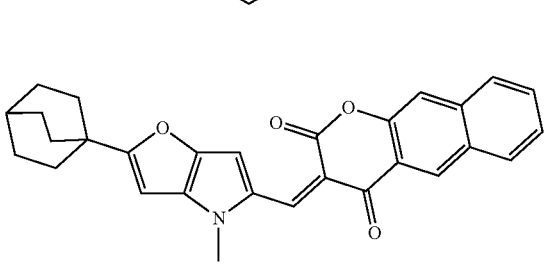
-continued
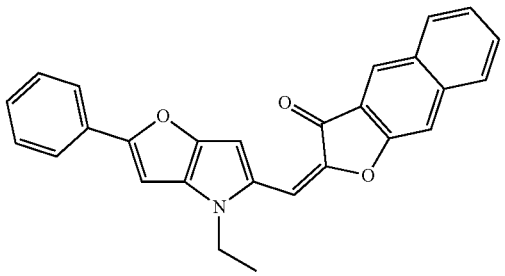
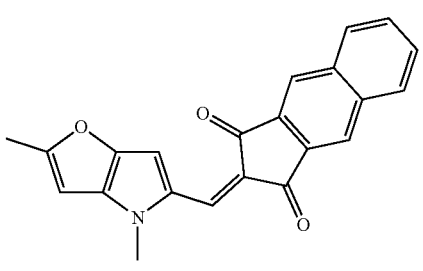
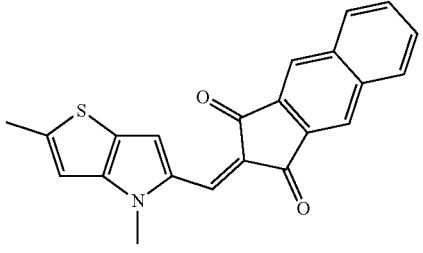
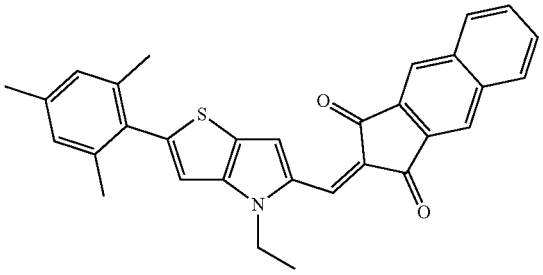
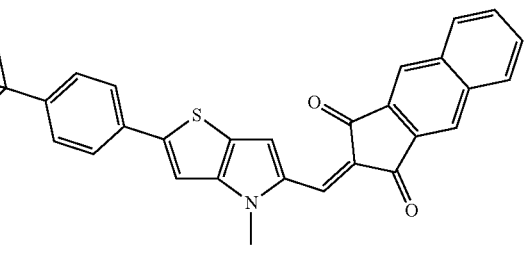
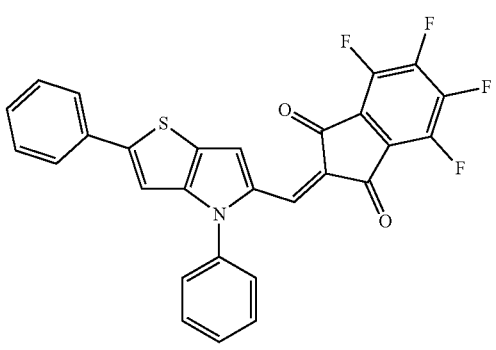

27
-continued
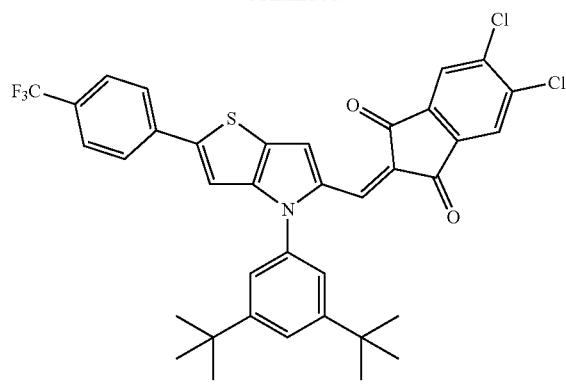
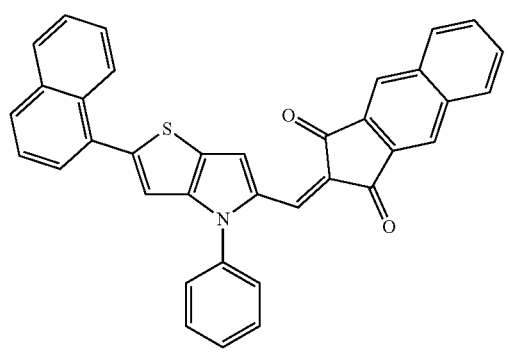
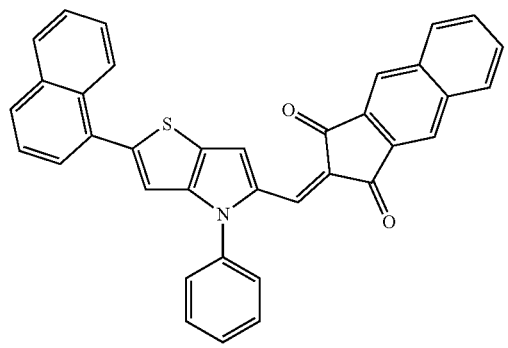
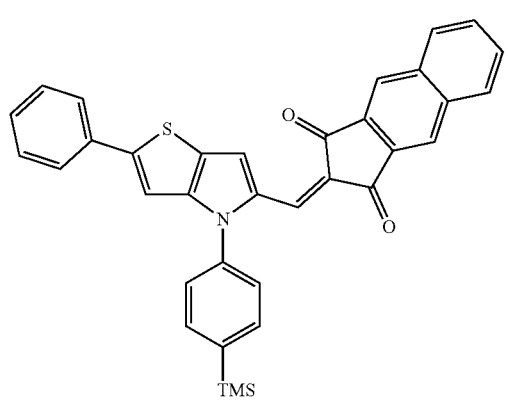
28
-continued
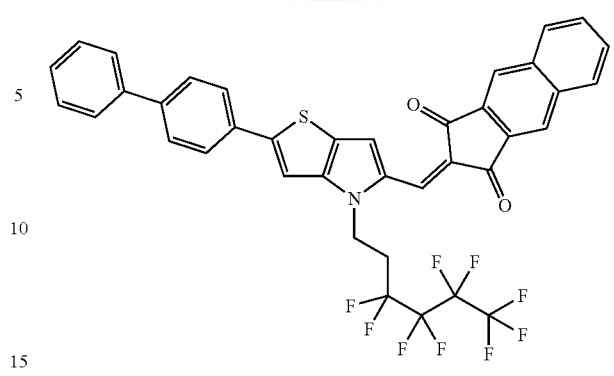
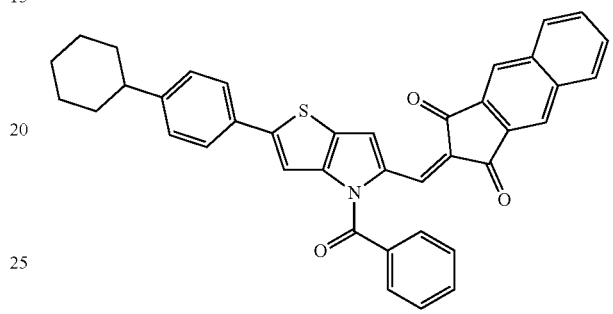
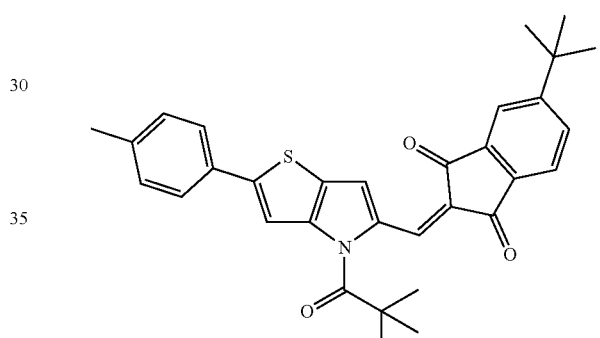
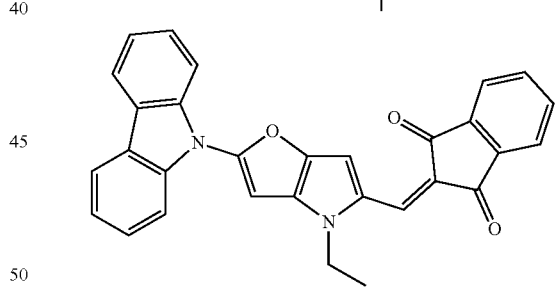
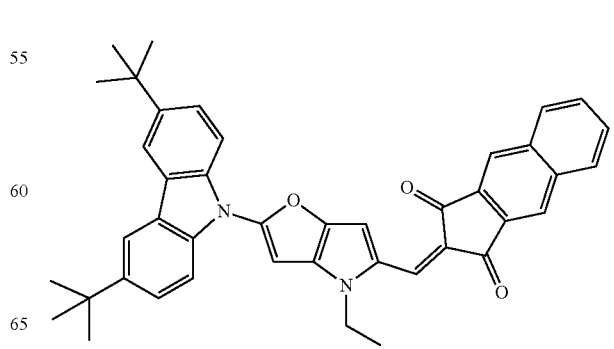

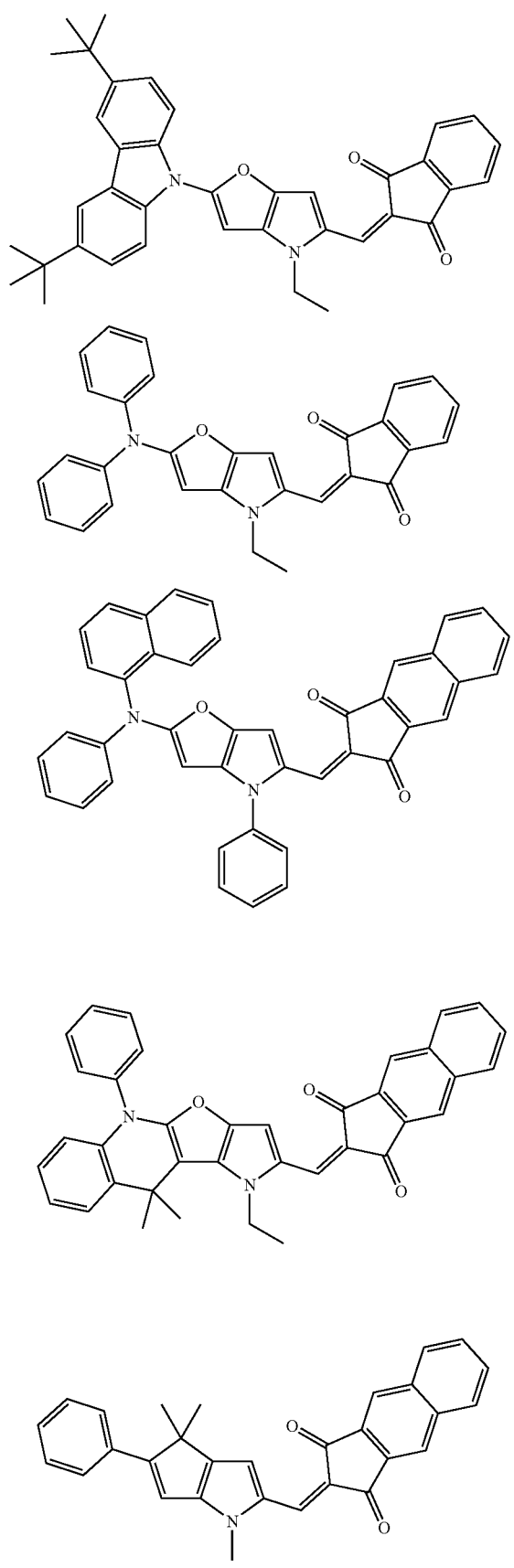
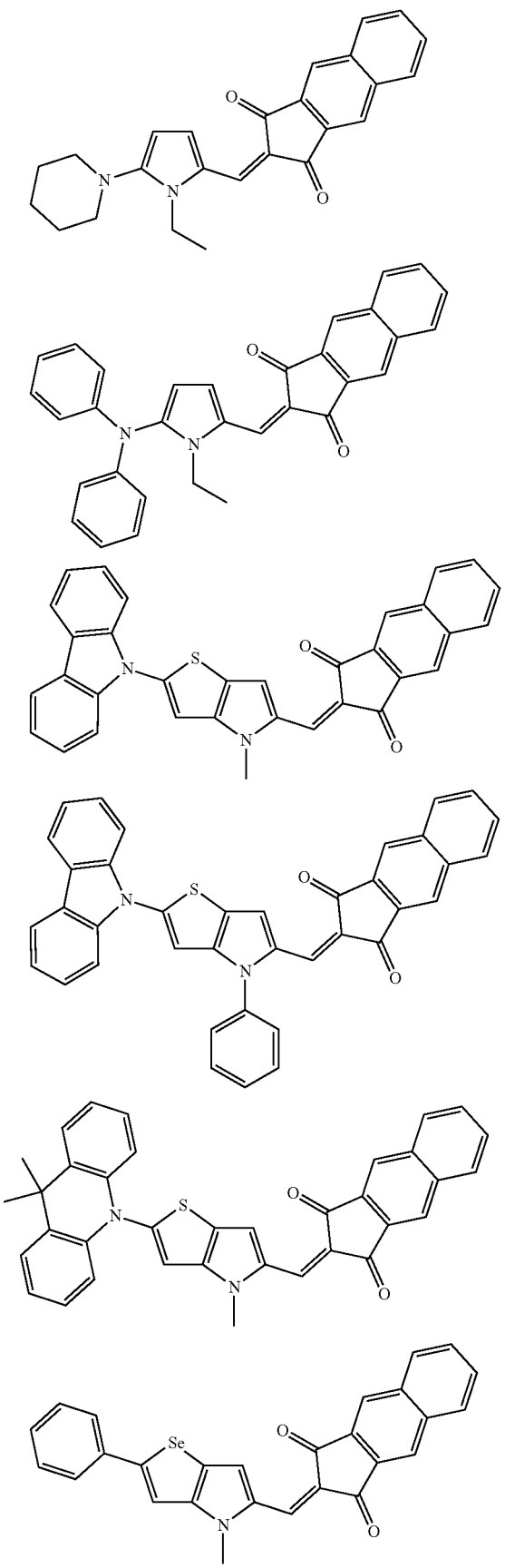

31
-continued
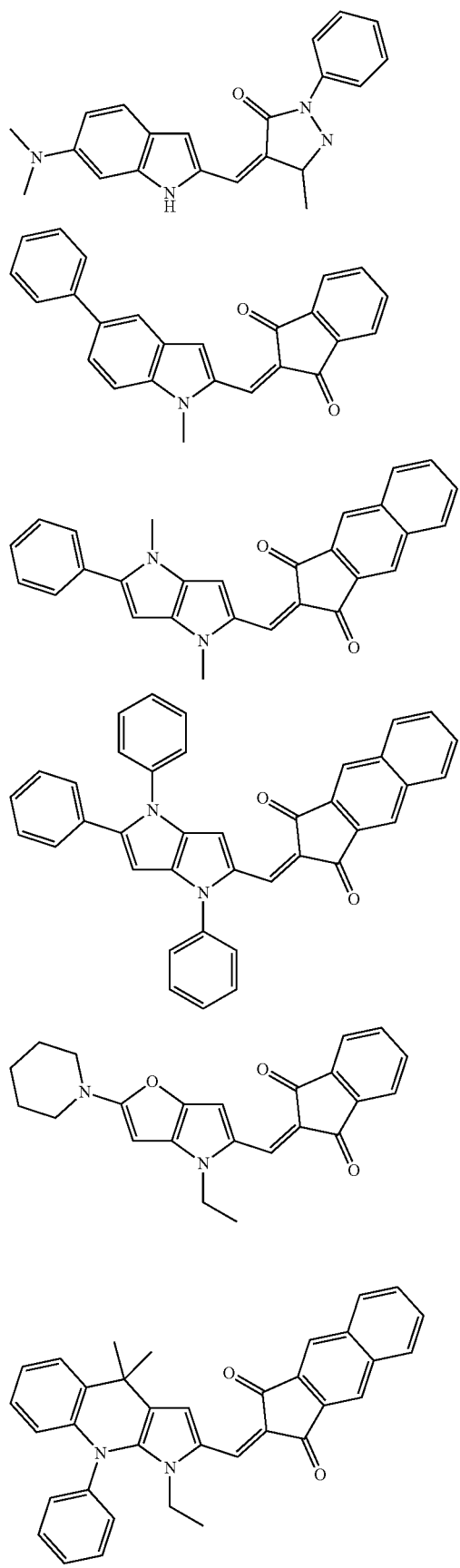
32
-continued
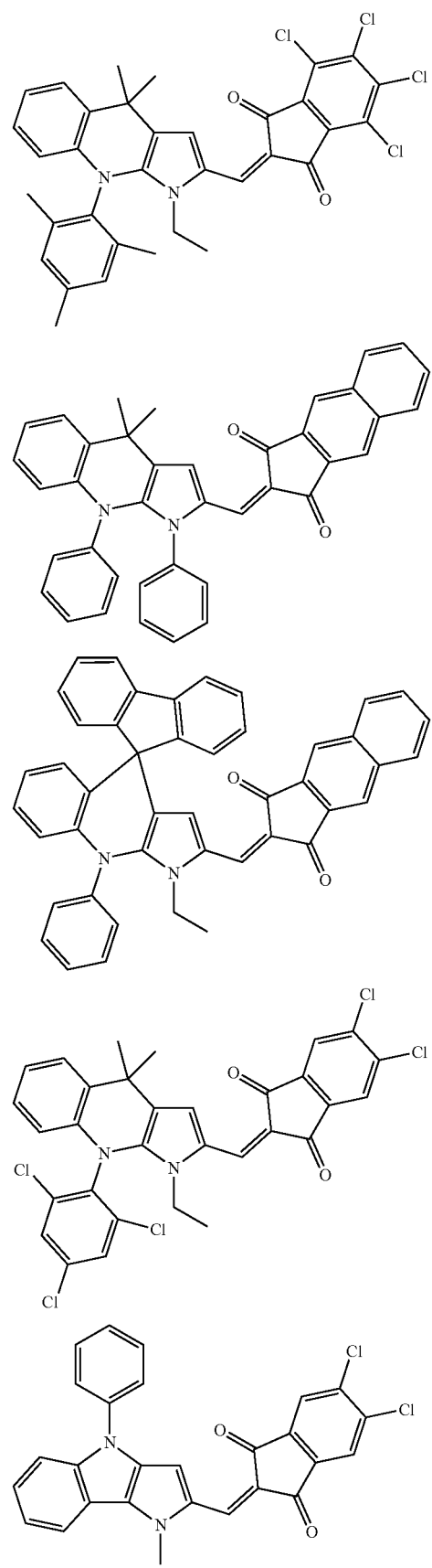

-continued

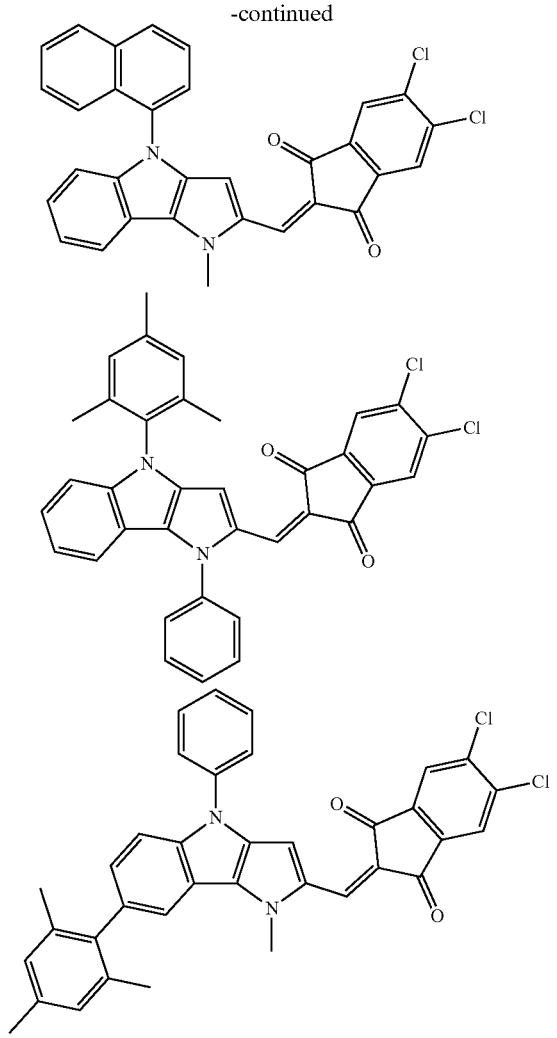

A molecular weight of the specific compound is not particularly limited, but is preferably 300 to 900. In a case where the molecular weight is 900 or less, the vapor deposition temperature does not increase, and the decomposition of the compound hardly occurs. In a case where the molecular weight is 300 or more, a glass transition point of a deposited film does not decrease, and a heat resistance of the photoelectric conversion element is improved.

The specific compound is particularly useful as a material of the photoelectric conversion film used for the optical sensor, the imaging element, or a photoelectric cell. In addition, the specific compound usually functions as the p-type organic semiconductor in the photoelectric conversion film in many cases. The specific compound can also be used as a coloring material, a liquid crystal material, an organic semiconductor material, a charge transport material, a pharmaceutical material, and a fluorescent diagnostic material.

The specific compound is preferably a compound in which an ionization potential in a single film is −5.0 to −6.0 eV from the viewpoints of stability in a case of using the compound as the p-type organic semiconductor and matching of energy levels between the compound and the n-type organic semiconductor.

In order to be applicable to the organic photoelectric conversion film 209 that absorbs green light and performs photoelectric conversion, the maximum absorption wavelength of the specific compound is preferably in the range of 450 to 600 nm, and is more preferably in the range of 480 to 600 nm.

The maximum absorption wavelength is a value measured in a solution state (solvent: chloroform) by adjusting the absorption spectrum of the specific compound to a concentration such that the light absorbance is 0.5 to 1.

<n-Type Organic Semiconductor>

It is preferable that the photoelectric conversion film contains the n-type organic semiconductor as a component other than the specific compound.

The n-type organic semiconductor is an acceptor-property organic semiconductor material (a compound), and refers to an organic compound having a property of easily accepting an electron. More specifically, the n-type organic semiconductor refers to an organic compound having a large electron affinity of two organic compounds used in contact with each other.

Examples of the n-type organic semiconductor include a condensed aromatic carbocyclic compound (for example, fullerene, a naphthalene derivative, an anthracene derivative, a phenanthrene derivative, a tetracene derivative, a pyrene derivative, a perylene derivative, and a fluoranthene derivative); a 5 to 7 membered heterocyclic compound having at least one of a nitrogen atom, an oxygen atom, or a sulfur atom (for example, pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, and thiazole); a polyarylene compound; a fluorene compound; a cyclopentadiene compound; a silyl compound; and a metal complex having a nitrogen-containing heterocyclic compound as the ligands.

An organic dye may be used as the n-type organic semiconductor. Examples of the organic dye include a cyanine dye, a styryl dye, a hemicyanine dye, a merocyanine dye (including zeromethine merocyanine (simple merocyanine)), a rhodacyanine dye, an allopolar dye, an oxonol dye, a hemioxonol dye, a squarylium dye, a croconium dye, an azamethine dye, a coumarin dye, an arylidene dye, an anthraquinone dye, a triphenylmethane dye, an azo dye, an azomethine dye, a metallocene dye, a fluorenone dye, a flugide dye, a perylene dye, a phenazine dye, a phenothiazine dye, a quinone dye, a diphenylmethane dye, a polyene dye, an acridine dye, an acridinone dye, a diphenylamine dye, a quinophthalone dye, a phenoxazine dye, a phthaloperylene dye, a dioxane dye, a porphyrin dye, a chlorophyll dye, a phthalocyanine dye, a subphthalocyanine dye, and a metal complex dye.

The molecular weight of the n-type organic semiconductor is preferably 200 to 1200, and more preferably 200 to 900.

On the other hand, in a case of the form as shown in FIG. 2, it is desirable that the n-type organic semiconductor is colorless, or has the maximum absorption wavelength and/or an absorption waveform close to that of the specific compound, and a specific value of the maximum absorption wavelength of the n-type organic semiconductor is desirably 400 nm or less, or 500 to 600 nm.

It is preferable that the photoelectric conversion film has a bulk hetero structure formed in a state in which the specific compound and the n-type organic semiconductor are mixed. The bulk hetero structure refers to a layer in which the specific compound and the n-type organic semiconductor are mixed and dispersed in the photoelectric conversion film. The photoelectric conversion film having the bulk hetero structure can be formed by either a wet method or a dry method. The bulk hetero structure is described in detail in, for example, paragraphs [0013] to [0014] of JP2005-303266A.

The content of the specific compound to the total content of the specific compound and the n-type organic semiconductor (=film thickness in terms of single layer of specific compound/(film thickness in terms of single layer of specific compound+film thickness in terms of single layer of n-type organic semiconductor)×100) is preferably 20 to 80 volume %, more preferably 30 to 70 volume %, and still more preferably 40 to 60 volume % from the viewpoint of responsiveness of the photoelectric conversion element.

It is preferable that the photoelectric conversion film is substantially formed of the specific compound and the n-type organic semiconductor. The term "substantially" means that the total content of the specific compound and the n-type organic semiconductor to the total mass of the photoelectric conversion film is 95 mass % or more.

The n-type organic semiconductor contained in the photoelectric conversion film may be used alone, or by a combination of two or more types.

The photoelectric conversion film may further contain a p-type organic semiconductor in addition to the specific compound and the n-type organic semiconductor. Examples of the p-type organic semiconductor include examples shown below.

In a case where the specific compound is used as the p-type organic semiconductor, the p-type organic semiconductor intends the p-type organic semiconductor other than the specific compound.

<p-Type Organic Semiconductor>

The p-type organic semiconductor is a donor-property organic semiconductor material (a compound), and refers to an organic compound having a property of easily donating an electron. More specifically, the p-type organic semiconductor refers to an organic compound having an ionization potential of two organic compounds used in contact with each other.

Examples of the p-type organic semiconductor (the p-type organic semiconductor other than the specific compound) include a triarylamine compound, a benzidine compound, a pyrazoline compound, a styrylamine compound, a hydrazone compound, a carbazole compound, a polysilane compound, a thiophene compound, a cyanine compound, an oxonol compound, a polyamine compound, an indole compound, a pyrrole compound, a pyrazole compound, a polyarylene compound, a condensed aromatic carbocyclic compound, and metal complexes having a nitrogen-containing heterocyclic compound as ligands.

Examples of the p-type organic semiconductor include a compound having an ionization potential smaller than that of the n-type organic semiconductor. When this condition is satisfied, the organic dye exemplified as the n-type organic semiconductor can be used.

The photoelectric conversion film containing the specific compound is a non-luminescent film, and has a feature different from an organic light emitting diode (OLED). The non-luminescent film means a film having a luminescence quantum efficiency of 1% or less, and the luminescence quantum efficiency is preferably 0.5% or less, and more preferably 0.1% or less.

<Film Formation Method>

The photoelectric conversion film can be formed mostly by a dry film formation method. Specific examples of the dry film formation method include a physical vapor deposition method such as a vapor deposition method (in particular, a vacuum evaporation method), a sputtering method, an ion plating method, and molecular beam epitaxy (MBE), and chemical vapor deposition (CVD) such as plasma polymerization. Among these, the vacuum evaporation method is preferable. In a case where the photoelectric conversion film is formed by the vacuum evaporation method, a producing condition such as a degree of vacuum and a vapor deposition temperature can be set according to the normal method.

The thickness of the photoelectric conversion film is preferably 10 to 1000 nm, more preferably 50 to 800 nm, still more preferably 50 to 500 nm, and particularly preferably 50 to 300 nm.

[Electrode]

The electrode (the upper electrode (the transparent conductive film) 15 and the lower electrode (the conductive film) 11) is formed of a conductive material. Examples of the conductive material include metals, alloys, metal oxides, electrically conductive compounds, and mixtures thereof.

Since light is incident through the upper electrode 15, the upper electrode 15 is preferably transparent to light to be detected. Examples of the material forming the upper electrode 15 include conductive metal oxides such as tin oxide (ATO, FTO) doped with antimony, fluorine, or the like, tin oxide, zinc oxide, indium oxide, indium tin oxide (ITO), and indium zinc oxide (IZO); metal thin films such as gold, silver, chromium, and nickel; mixtures or laminates of these metals and the conductive metal oxides; and organic conductive materials such as polyaniline, polythiophene, and polypyrrole. Among these, conductive metal oxides are preferable from the viewpoints of high conductivity, transparency, and the like.

In general, in a case where the conductive film is made to be thinner than a certain range, a resistance value is rapidly increased. However, in the solid-state imaging element into which the photoelectric conversion element according to the present embodiment is incorporated, the sheet resistance is preferably 100 to 10000Ω/□, and the degree of freedom of the range of the film thickness that can be thinned is large. In addition, as the thickness of the upper electrode (the transparent conductive film) 15 is thinner, the amount of light that the upper electrode absorbs becomes smaller, and the light transmittance usually increases. The increase in the light transmittance causes an increase in light absorbance in the photoelectric conversion film and an increase in the photoelectric conversion ability, which is preferable. Considering the suppression of leakage current, an increase in the resistance value of the thin film, and an increase in transmittance accompanied by the thinning, the film thickness of the upper electrode 15 is preferably 5 to 100 nm, and more preferably 5 to 20 nm.

There is a case where the lower electrode 11 has transparency or an opposite case where the lower electrode does not have transparency and reflects light, depending on the application. Examples of a material constituting the lower electrode 11 include conductive metal oxides such as tin oxide (ATO, FTO) doped with antimony, fluorine, or the like, tin oxide, zinc oxide, indium oxide, indium tin oxide (ITO), and indium zinc oxide (IZO); metals such as gold, silver, chromium, nickel, titanium, tungsten, and aluminum, conductive compounds (for example, titanium nitride (TiN)) such as oxides or nitrides of these metals; mixtures or laminates of these metals and conductive metal oxides; and organic conductive materials such as polyaniline, polythiophene, and polypyrrole.

The method of forming electrodes is not particularly limited, and can be appropriately selected in accordance with the electrode material. Specific examples thereof include a wet method such as a printing method and a coating method; a physical method such as a vacuum evaporation method, a sputtering method, and an ion plating method; and a chemical method such as a CVD method and a plasma CVD method.

In a case where the material of the electrode is ITO, examples thereof include an electron beam method, a sputtering method, a resistance thermal vapor deposition method, a chemical reaction method (such as a sol-gel method), and a coating method with a dispersion of indium tin oxide.

[Charge Blocking Film: Electron Blocking Film and Positive Hole Blocking Film]

It is also preferable that the photoelectric conversion element of the embodiment of the invention has one or more interlayers between the conductive film and the transparent conductive film, in addition to the photoelectric conversion film. Example of the interlayer includes the charge blocking film. In the case where the photoelectric conversion element has this film, the characteristics (such as photoelectric conversion efficiency and responsiveness) of the photoelectric conversion element to be obtained become superior. Examples of the charge blocking film include the electron blocking film and the positive hole blocking film. Hereinafter, the films will be described in detail.

<Electron Blocking Film>

The electron blocking film includes an electron donating compound. Specific examples of a low molecular material include aromatic diamine compounds such as N,N'-bis(3-methylphenyl)-(1,1'-biphenyl)-4,4'-diamine (TPD) and 4,4'-bis[N-(naphthyl)-N-phenyl-amino]biphenyl ($\alpha$-NPD); porphyrin compounds such as porphyrin, copper tetraphenylporphyrin, phthalocyanine, copper phthalocyanine, and titanium phthalocyanine oxide; and oxazole, oxadiazole, triazole, imidazole, imidazolone, a stilbene derivative, a pyrazoline derivative, tetrahydroimidazole, polyarylalkane, butadiene, 4,4',4''-tris(N-(3-methylphenyl)-N-phenylamino) triphenylamine (m-MTDATA), a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, and a silazane derivative. Specific examples of a polymer material include a polymer such as phenylenevinylene, fluorene, carbazole, indole, pyrene, pyrrole, picoline, thiophene, acetylene, and diacetylene, and a derivative thereof. In addition, compounds described in paragraphs [0049] to [0063] of JP5597450B, compounds described in paragraphs [0119] to [0158] of JP2011-225544A, and compounds described in paragraphs [0086] to [0090] of JP2012-094660A are exemplified.

The electron blocking film may be configured by a plurality of films.

The electron blocking film may be formed of an inorganic material. In general, an inorganic material has a dielectric constant larger than that of an organic material. Therefore, in a case where the inorganic material is used in the electron blocking film, a large voltage is applied to the photoelectric conversion film. Therefore, the photoelectric conversion efficiency increases. Examples of the inorganic material that can be used in the electron blocking film include calcium oxide, chromium oxide, copper chromium oxide, manganese oxide, cobalt oxide, nickel oxide, copper oxide, copper gallium oxide, copper strontium oxide, niobium oxide, molybdenum oxide, copper indium oxide, silver indium oxide, and iridium oxide.

(Positive Hole Blocking Film)

The positive hole blocking film includes an electron accepting compound.

Examples of the electron accepting compound include an oxadiazole derivative such as 1,3-bis(4-tert-butylphenyl-1,3,4-oxadiazolyl)phenylene (OXD-7); an anthraquinodimethane derivative; a diphenylquinone derivative; bathocuproine, bathophenanthroline, and derivatives thereof; a triazole compound; a tris(8-hydroxyquinolinato)aluminum complex; a bis(4-methyl-8-quinolinato)aluminum complex; a distyrylarylene derivative; and a silole compound. In addition, compounds described in paragraphs [0056] to [0057] of JP2006-100767A are exemplified.

The method of producing the charge blocking film is not particularly limited, a dry film formation method and a wet film formation method are exemplified. Examples of the dry film formation method include a vapor deposition method and a sputtering method. The vapor deposition method may be any of physical vapor deposition (PVD) method and chemical vapor deposition (CVD) method, and physical vapor deposition method such as vacuum evaporation method is preferable. Examples of the wet film formation method include an inkjet method, a spray method, a nozzle printing method, a spin coating method, a dip coating method, a casting method, a die coating method, a roll coating method, a bar coating method, and a gravure coating method, and an inkjet method is preferable from the viewpoint of high precision patterning.

Each thickness of the charge blocking films (the electron blocking film and the positive hole blocking film) is preferably 3 to 200 nm, more preferably 5 to 100 nm, and still more preferably 5 to 30 nm.

[Substrate]

The photoelectric conversion element may further include a substrate. The type of substrate to be used is not particularly limited, and a semiconductor substrate, a glass substrate, and a plastic substrate are exemplified.

The position of the substrate is not particularly limited, but in general, the conductive film, the photoelectric conversion film, and the transparent conductive film are laminated on the substrate in this order.

[Sealing Layer]

The photoelectric conversion element may further include a sealing layer. The performance of the photoelectric conversion material may deteriorate noticeably due to the presence of deterioration factors such as water molecules. The deterioration can be prevented by sealing and coating the entirety of the photoelectric conversion film with the sealing layer such as diamond-like carbon (DLC) or ceramics such as metal oxide, or metal nitride, and metal nitride oxide which are dense and into which water molecules do not permeate.

The material of the sealing layer may be selected and the sealing layer may be produced according to the description in paragraphs [0210] to [0215] of JP2011-082508A.

[Optical Sensor]

Examples of the application of the photoelectric conversion element include the photoelectric cell and the optical sensor, but the photoelectric conversion element of the embodiment of the invention is preferably used as the optical sensor. The photoelectric conversion element may be used alone as the optical sensor. Alternately, the photoelectric conversion element may be used as a line sensor in which the photoelectric conversion elements are linearly arranged or as a two-dimensional sensor in which the photoelectric conversion elements are planarly arranged. In the line sensor of the embodiment of the invention, the photoelectric conversion element of the invention functions as the imaging element by converting optical image information into an electric signal using an optical system such as a scanner, and a driving unit. In the two-dimensional sensor, the photoelectric conversion element of the invention functions as the imaging element by converting the optical image information into the electric signal by imaging the optical image information on the sensor using the optical system such as an imaging module.

[Imaging Element]

Next, a configuration example of an imaging element comprising the photoelectric conversion element 10a will be described.

In the configuration example which will be described below, the same reference numerals or the corresponding reference numerals are attached to members or the like having the same configuration or action as those which have already been described, to simplify or omit the description.

The imaging element is an element that converts optical information of an image into the electric signal, and is an element in which a plurality of photoelectric conversion elements are arranged on a matrix in the same planar form, optical signals are converted into electric signals in each photoelectric conversion element (a pixel), and the electric signals can be sequentially output to the outside of the imaging elements for each pixel. For this reason, one pixel is formed of one photoelectric conversion element and one or more transistors.

Figure 3:
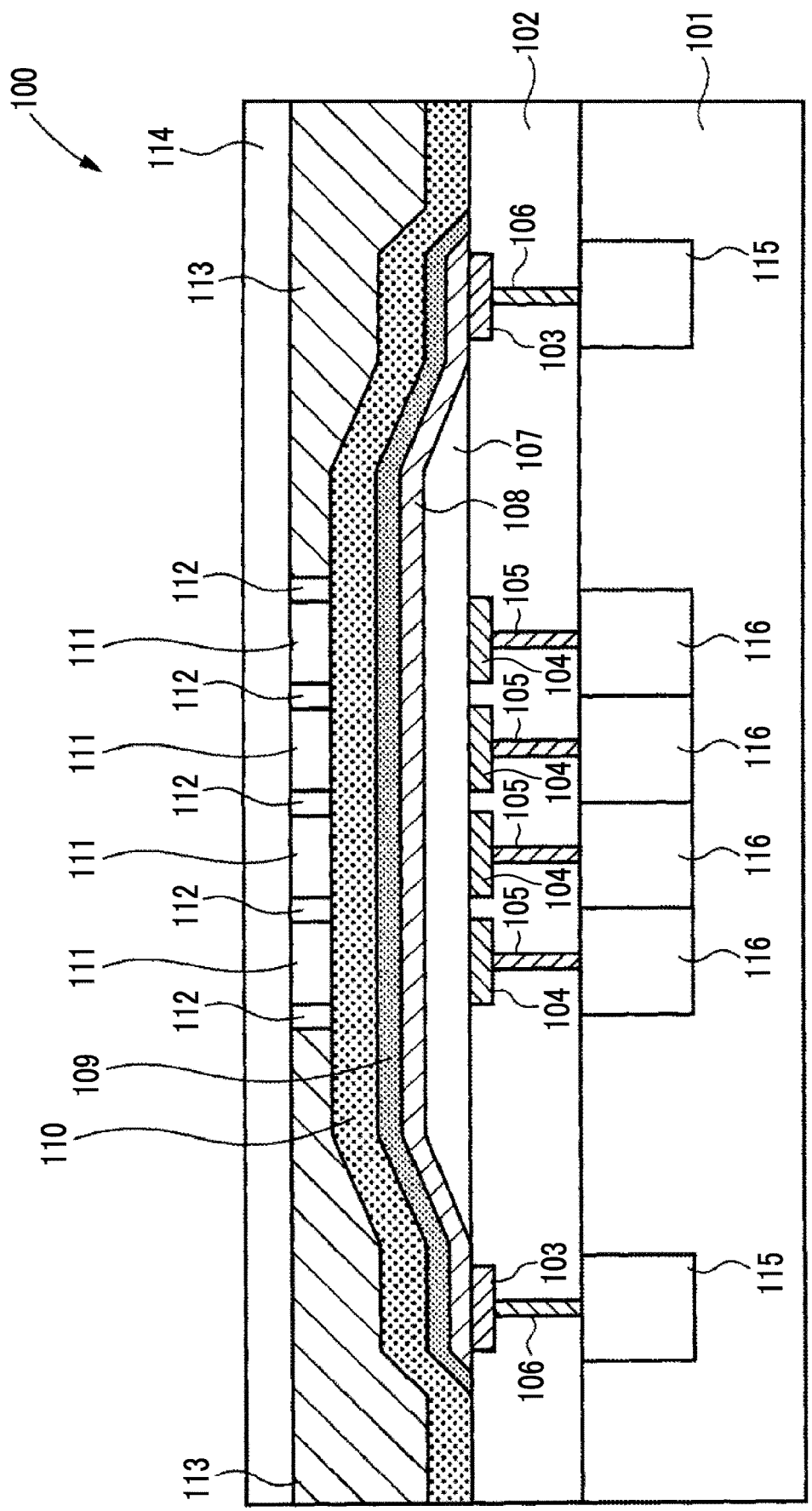
FIG. 3 is a schematic cross-sectional view of one pixel of an imaging element.

FIG. 3 is a schematic cross-sectional view showing a schematic configuration of an imaging element for describing an embodiment of the invention. This imaging element is mounted on an imaging device such as a digital camera and a digital video camera, an electronic endoscope, and imaging modules such as a cellular phone.

The imaging element has a plurality of photoelectric conversion elements having configurations shown in FIG. 1A and a circuit substrate in which the readout circuit reading out signals corresponding to charges generated in the photoelectric conversion film of each photoelectric conversion element is formed. The imaging element has a configuration in which the plurality of photoelectric conversion elements are one-dimensionally or two-dimensionally arranged on the same surface above the circuit substrate.

An imaging element 100 shown in FIG. 3 comprises a substrate 101, an insulating layer 102, connection electrodes 103, pixel electrodes (lower electrodes) 104, connection units 105, connection units 106, a photoelectric conversion film 107, a counter electrode (upper electrode) 108, a buffer layer 109, a sealing layer 110, a color filter (CF) 111, partition walls 112, a light shielding layer 113, a protective layer 114, a counter electrode voltage supply unit 115, and readout circuits 116.

The pixel electrode 104 has the same function as the lower electrode 11 of the photoelectric conversion element 10a shown in FIG. 1A. The counter electrode 108 has the same function as the upper electrode 15 of the photoelectric conversion element 10a shown in FIG. 1A. The photoelectric conversion film 107 has the same configuration as a layer provided between the lower electrode 11 and the upper electrode 15 of the photoelectric conversion element 10a shown in FIG. 1A.

The substrate 101 is a semiconductor substrate such as the glass substrate, or Si. The insulating layer 102 is formed on the substrate 101. A plurality of pixel electrodes 104 and a plurality of connection electrodes 103 are formed on the surface of the insulating layer 102.

The photoelectric conversion film 107 is a layer common to all the photoelectric conversion elements provided so as to cover the plurality of pixel electrodes 104.

The counter electrode 108 is one electrode common to all the photoelectric conversion elements provided on the photoelectric conversion film 107. The counter electrode 108 is formed on the connection electrodes 103 arranged on an outer side than the photoelectric conversion film 107, and is electrically connected to the connection electrodes 103.

The connection units 106 are buried in the insulating layer 102, and are plugs for electrically connecting the connection electrodes 103 to the counter electrode voltage supply unit 115. The counter electrode voltage supply unit 115 is formed in the substrate 101, and applies a predetermined voltage to the counter electrode 108 via the connection units 106 and the connection electrodes 103. In a case where a voltage to be applied to the counter electrode 108 is higher than a power supply voltage of the imaging element, the power supply voltage is boosted by a boosting circuit such as a charge pump to supply the predetermined voltage.

The readout circuits 116 are provided on the substrate 101 corresponding to each of the plurality of pixel electrodes 104, and read out signals corresponding to charges trapped by the corresponding pixel electrodes 104. The readout circuits 116 are configured, for example, of CCD and CMOS circuits, or a thin film transistor (TFT) circuit, and are shielded by the light shielding layer not shown in the drawing which is disposed in the insulating layer 102. The readout circuits 116 are electrically connected to the corresponding the pixel electrodes 104 via the connection units 105.

The buffer layer 109 is formed on the counter electrode 108 so as to cover the counter electrode 108. The sealing layer 110 is formed on the buffer layer 109 so as to cover the buffer layer 109. The color filters 111 are formed on the sealing layer 110 at positions corresponding to each of the pixel electrodes 104. The partition walls 112 are provided between the color filters 111, and are used for improving the light transmittance of the color filters 111.

The light shielding layer 113 is formed on the sealing layer 110 in a region other than the region where the color filters 111 and the partition walls 112 are provided, and prevents light from being incident to the photoelectric conversion film 107 formed outside an effective pixel region. The protective layer 114 is formed on the color filters 111, the partition walls 112, and the light shielding layer 113, and protects the entirety of the imaging element 100.

In the imaging element 100 configured as described above, light which has entered is incident on the photoelectric conversion film 107, and charges are generated in the photoelectric conversion film. The positive holes among the generated charges are trapped by the pixel electrodes 104, and voltage signals corresponding to the amount are output to the outside of the imaging element 100 using the readout circuits 116.

A method of producing the imaging element 100 is as follows. The connection units 105 and 106, the plurality of connection electrodes 103, the plurality of pixel electrodes 104, and the insulating layer 102 are formed on the circuit substrate in which the counter electrode voltage supply unit 115 and the readout circuits 116 are formed. The plurality of pixel electrodes 104 are disposed, for example, on the surface of the insulating layer 102 in a square lattice shape.

Next, the photoelectric conversion film 107 is formed on the plurality of pixel electrodes 104, for example, by the vacuum evaporation method. Next, the counter electrode 108 is formed on the photoelectric conversion film 107 under vacuum, for example, by the sputtering method. Next, the buffer layer 109 and the sealing layer 110 are sequentially formed on the counter electrode 108, for example, by the vacuum evaporation method. Next, after the color filters 111, the partition walls 112, and the light shielding layer 113 are formed, the protective layer 114 is formed, and the production of the imaging element 100 is completed.

EXAMPLES

Examples will be shown below, but the invention is not limited thereto.

Synthesis of Compound (D-1)

A compound (D-1) was synthesized according to the following scheme. In the following, "Et" represents an ethyl group and "Ac" represents an acetyl group.

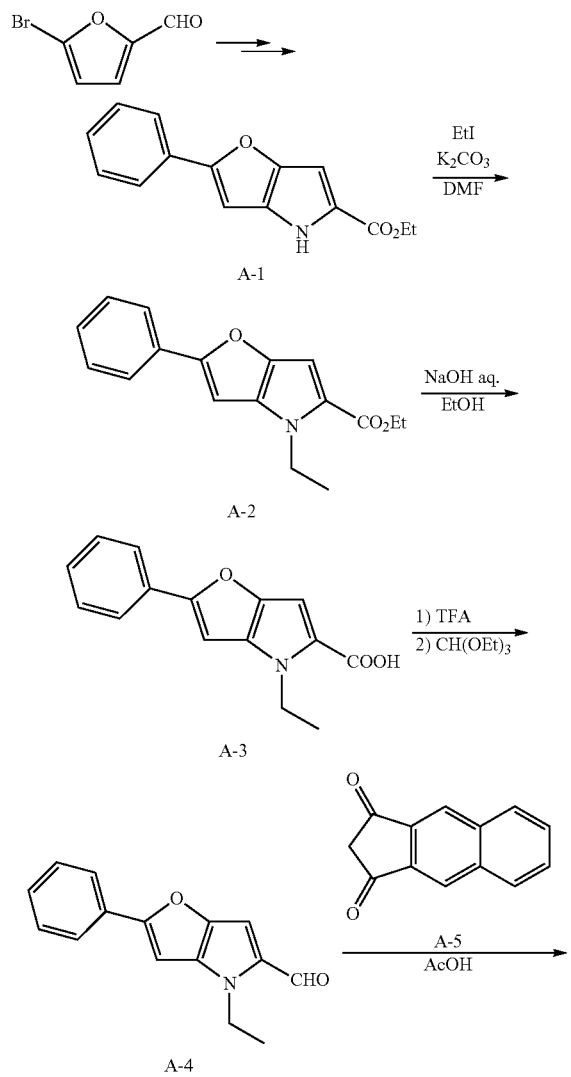

-continued

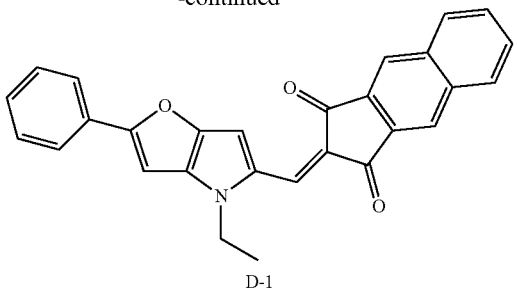

A compound (A-1) was synthesized from 2-bromo-5-furaldehyde according to the method disclosed in Chem. Eur. J. 2009, 15, 1096-1106.

The compound (A-1) (3.10 g, 10.9 mmol) was dissolved in N,N-dimethylformamide (DMF) (60 mL), iodoethane (5.08 g, 32.6 mmol) and potassium carbonate (6.23 g, 45.1 mmol) were added thereto, and the obtained mixed liquid was stirred with heating at 90° C. for 2 hours. After the mixed liquid was allowed to cool, the mixed liquid was added to water (300 mL) to precipitate a solid. The precipitated solid was filtered and washed with water. The obtained solid was vacuum dried to obtain a compound (A-2) (2.97 g, yield 96%).

The compound (A-2) (1.85 g, 5.90 mmol) was dissolved in ethanol (54 mL), a 1M aqueous sodium hydroxide solution (18 mL) was added thereto, and the obtained mixed liquid was reacted under heating reflux for 5 hours. After the mixed liquid was cooled to room temperature, a 1M aqueous hydrochloric acid solution was added until pH of the mixed liquid reached 1, and the solid was precipitated. The precipitated solid was filtered and washed with water. The obtained solid was vacuum dried to obtain a compound (A-3) (1.60 g, yield 95%).

The mixed liquid obtained by adding trifluoroacetic acid (TFA) (15 mL) to the compound (A-3) (4.40 g, 17.2 mmol) was reacted at room temperature for 15 minutes. Thereafter, ethyl orthoformate (5.0 mL) was added to the mixed liquid, and the mixed liquid was further reacted at room temperature for 15 minutes. The mixed liquid was added to a saturated aqueous sodium hydrogen carbonate solution (300 mL) and stirred for 30 minutes to precipitate a solid. The precipitated solid was filtered and washed with water. The obtained solid was vacuum dried to obtain a compound (A-4) (2.72 g, yield 66%).

A mixed liquid obtained by adding the compound (A-4) (1.30 g, 5.43 mmol) and a compound (A-5) (1.12 g, 5.70 mmol) to an acetic acid (40 mL) was reacted at 70° C. for 4 hours. After the mixed liquid was cooled to room temperature, methanol (80 mL) was added to the mixed liquid and stirred for 30 minutes to precipitate a solid. The precipitated solid was filtered and washed with methanol to obtain a crude product.

The obtained crude product was recrystallized from chlorobenzene (100 mL), and the solid obtained by recrystallization was washed with methanol to obtain the compound (D-1) (1.48 g, yield 65%). The obtained compound (D-1) was identified by a $^1$H nuclear magnetic resonance (NMR) and a mass spectrometry (MS).

Figure 4:
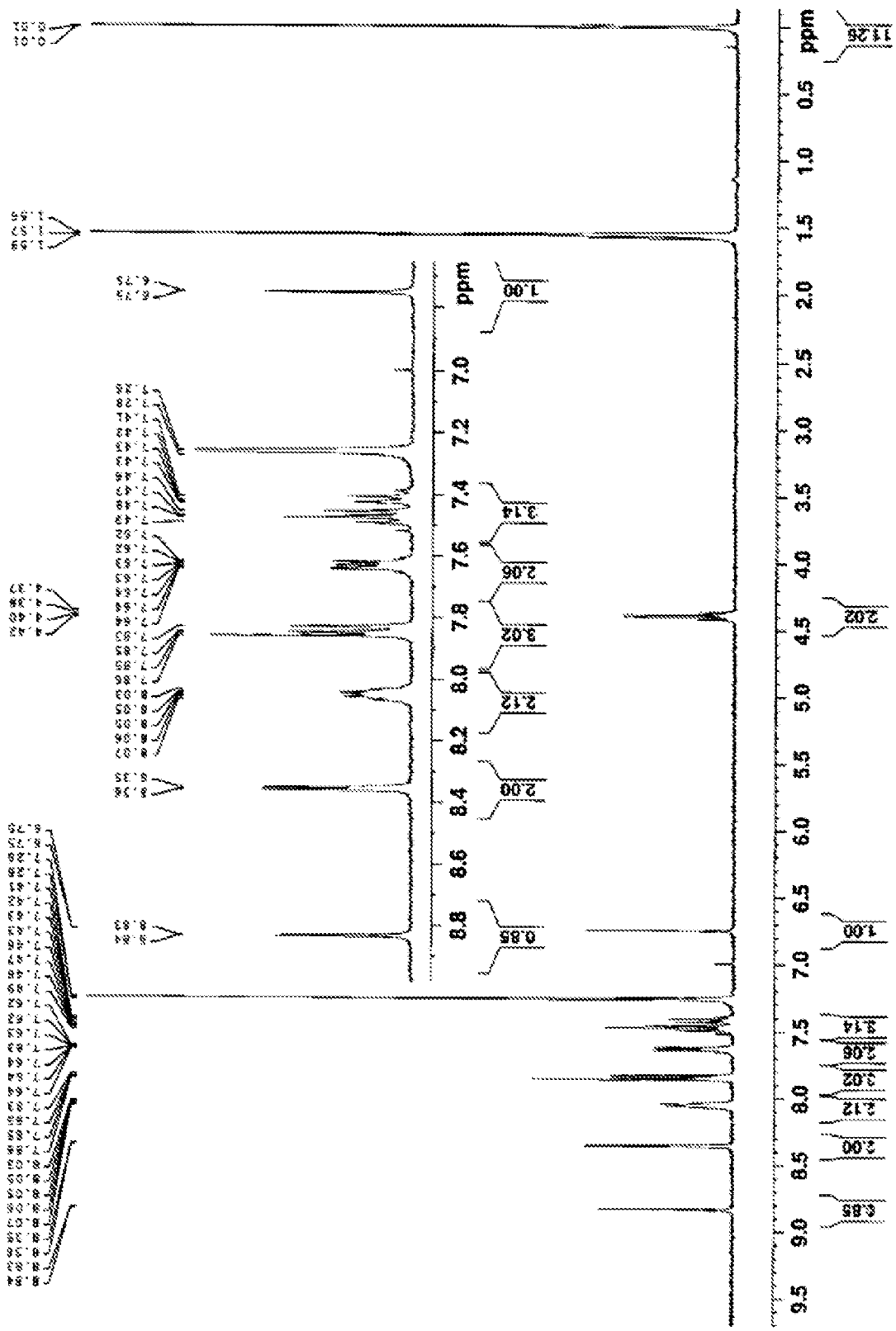
FIG. 4 is a $^1$H nuclear magnetic resonance (NMR) chart of a compound (D-1).

$^1$H NMR spectrum (400 MHz, CDCl$_3$) is shown in FIG. 4.

MS(ESI$^+$) m/z: 418.1 ([M+H]$^+$)

With reference to the synthesis method of the compound (D-1), compounds (D-2) to (D-24) were synthesized. The structures of the obtained compounds (D-1) to (D-24) and the comparative compounds (R-1) to (R-3) are specifically shown below.

Figure 5:
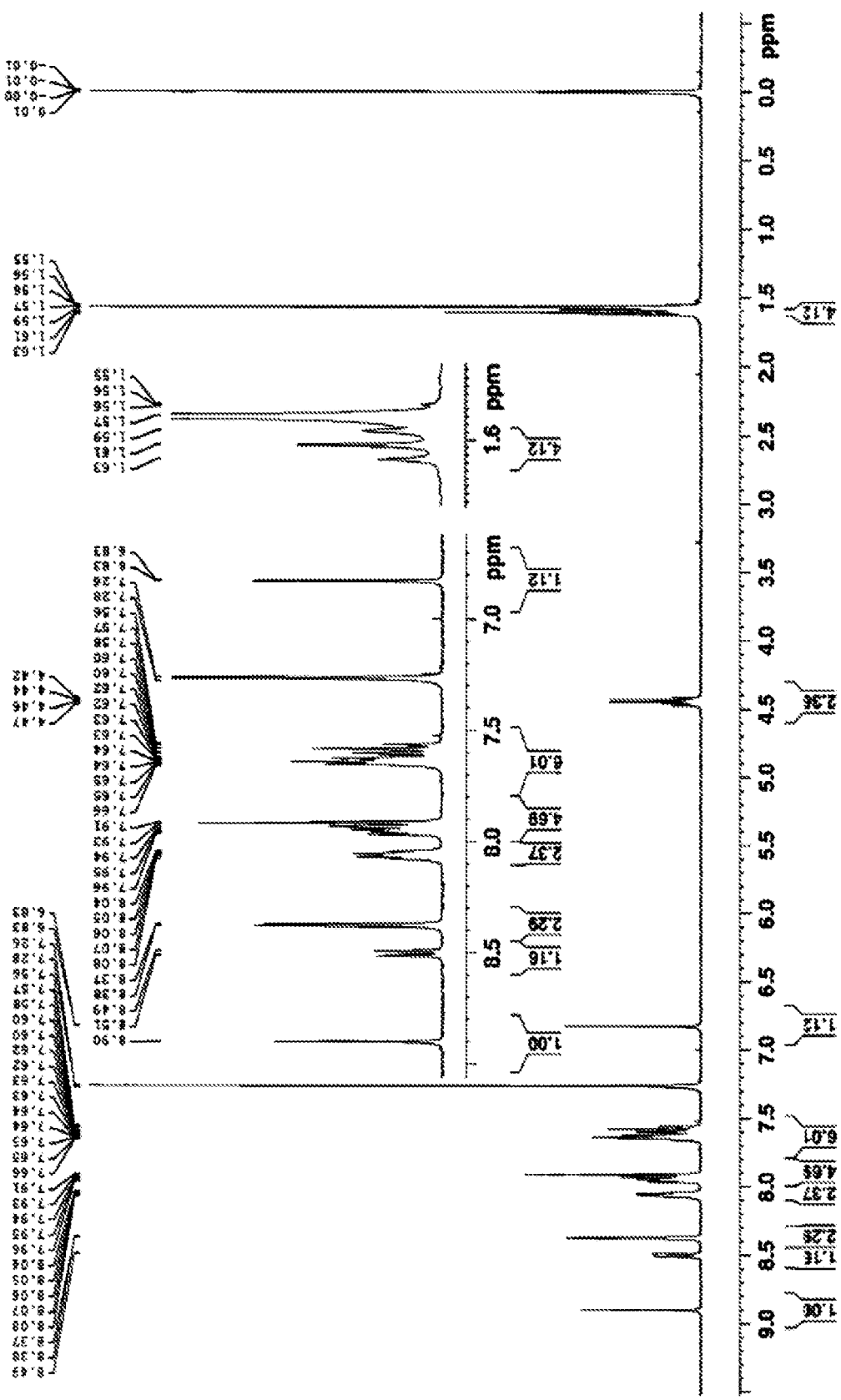
FIG. 5 is a $^1$H nuclear magnetic resonance (NMR) chart of a compound (D-3).
Figure 6:
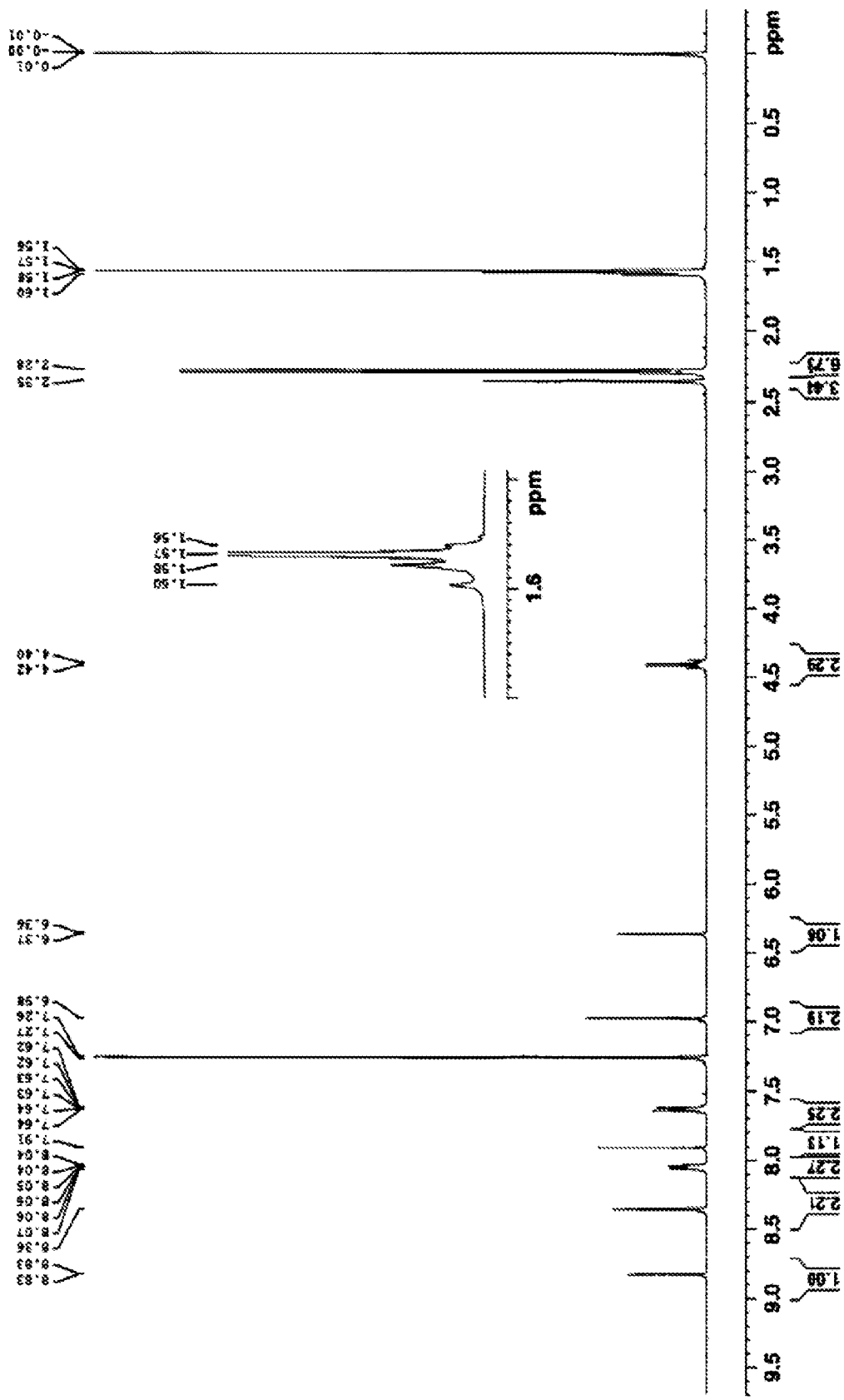
FIG. 6 is a $^1$H nuclear magnetic resonance (NMR) chart of a compound (D-4).

$^1$H NMR spectra (400 MHz, CDCl$_3$) of the compounds (D-3), (D-4), and (D-6) are shown in FIGS. 5 to 7.

In a case where the obtained compounds (D-1) to (D-24) were applied to Formula (1) or (2), the structural formula shown below intends to include both the cis isomer and the trans isomer which are distinguished based on a group corresponding to the C=C double bond constituted by a carbon atom to which R$^{a7}$ or R$^{b5}$ bonds and a carbon atom adjacent thereto.

D-1
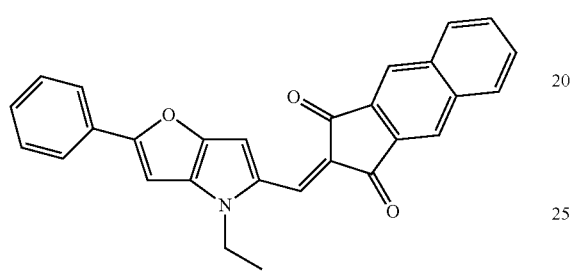

D-2
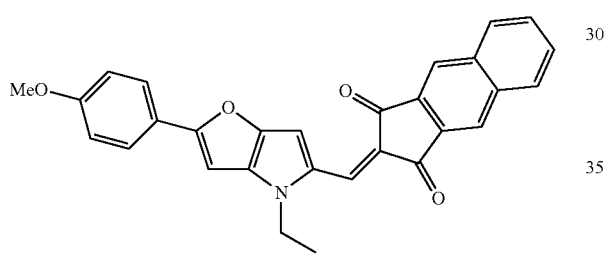

D-3
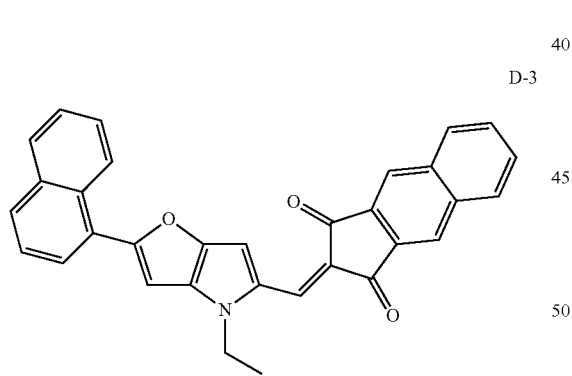

D-4
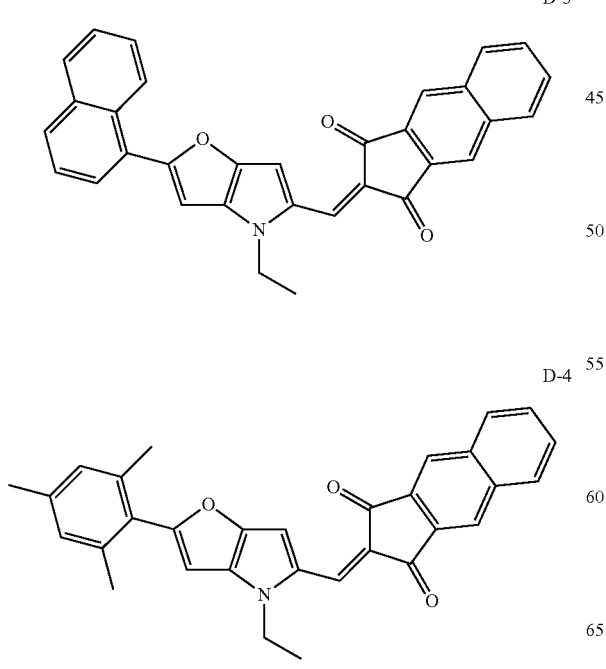

-continued

D-5
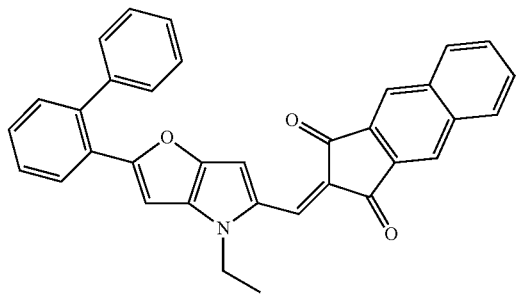

D-6
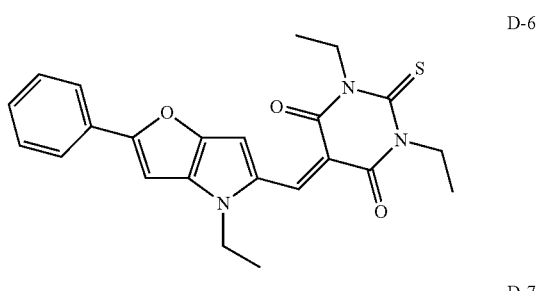

D-7
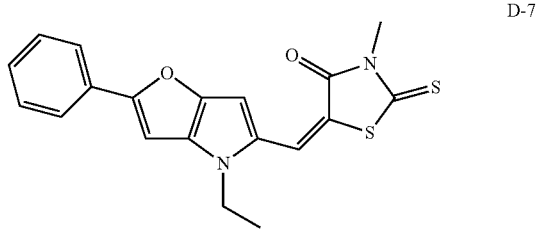

D-8
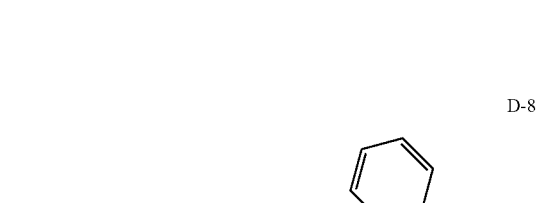

D-9
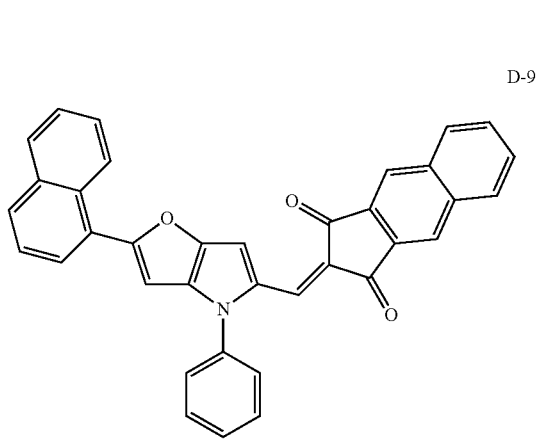

-continued
D-10
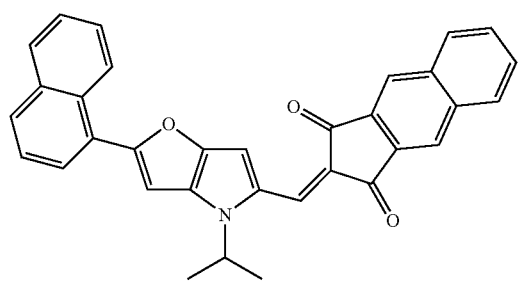
D-11
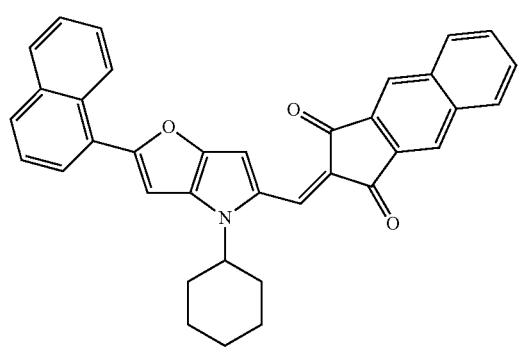
D-12
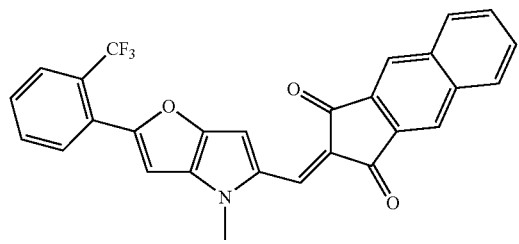
D-13
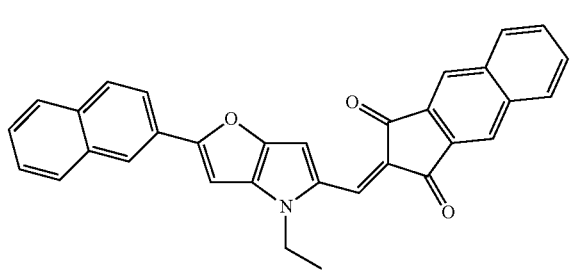
D-14
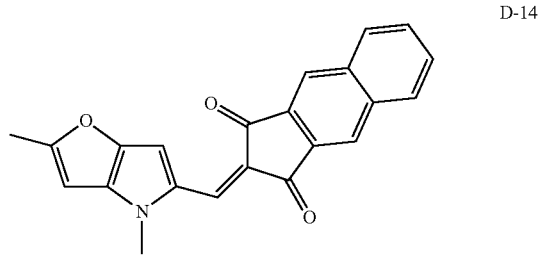
-continued
D-15
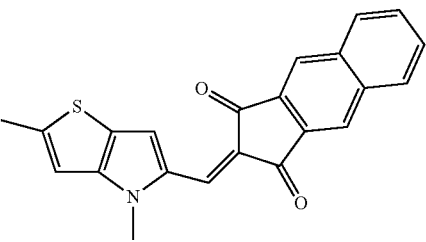
D-16
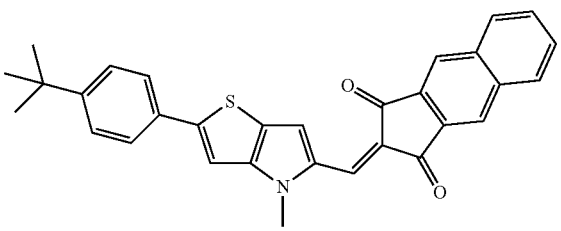
D-17
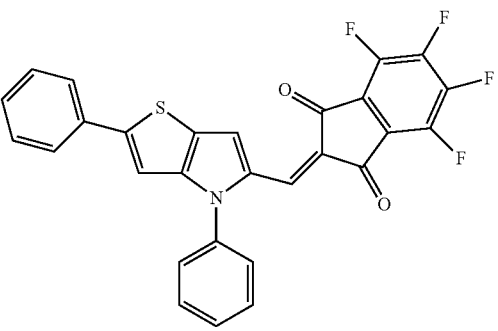
D-18
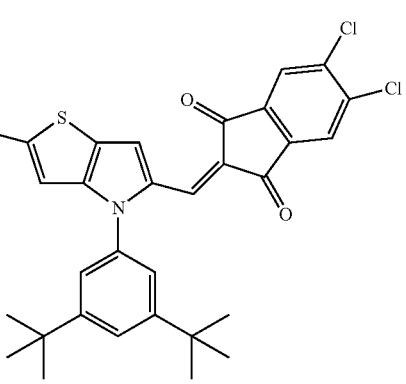
D-19
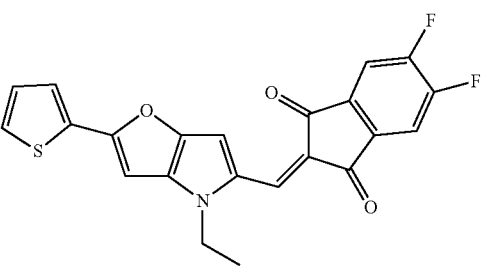

D-20
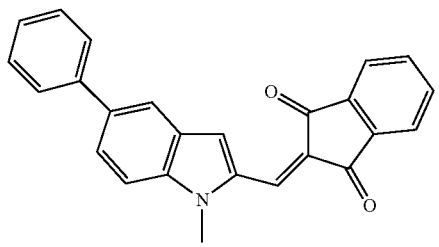

D-21
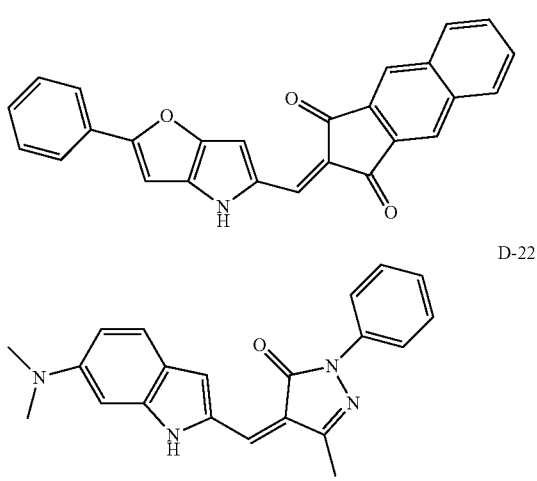

D-22

D-23

D-24

R-1
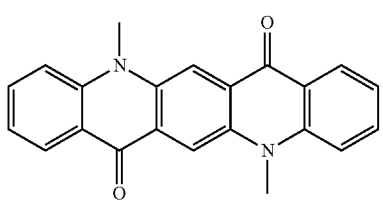

R-2
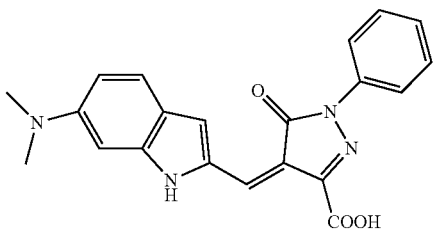

R-3

<Production of Reference Photoelectric Conversion Element>

The photoelectric conversion element of the form of FIG. 1A was produced using the obtained compound. In other words, the photoelectric conversion element to be evaluated in the present example is formed of the lower electrode 11, the electron blocking film 16A, the photoelectric conversion film 12, and the upper electrode 15.

Specifically, an amorphous ITO was formed into a film on the glass substrate by the sputtering method to form the lower electrode 11 (a thickness: 30 nm). Furthermore, the compound (EB-1) was formed into a film on the lower electrode 11 by the vacuum evaporation method to form the electron blocking film 16A (a thickness: 30 nm).

Furthermore, the compound (R-1) as the p-type organic semiconductor and the fullerene ($C_{60}$) as the n-type organic semiconductor were subjected to co-vapor deposition by the vacuum evaporation method so as to be respectively 100 nm in terms of single layer on the electron blocking film 16A to form a film in a state where the temperature of the substrate was controlled to 25° C., and the photoelectric conversion film 12 having the bulk hetero structure of 200 nm was formed. Furthermore, amorphous ITO was formed into a film on the photoelectric conversion film 12 by a sputtering method to form the upper electrode 15 (the transparent conductive film) (the thickness: 10 nm). After the SiO film was formed as the sealing layer on the upper electrode 15 by a vacuum evaporation method, an aluminum oxide ($Al_2O_3$) layer was formed thereon by an atomic layer chemical vapor deposition (ALCVD) method to produce a photoelectric conversion element.

The obtained photoelectric conversion element was to be an element (A).

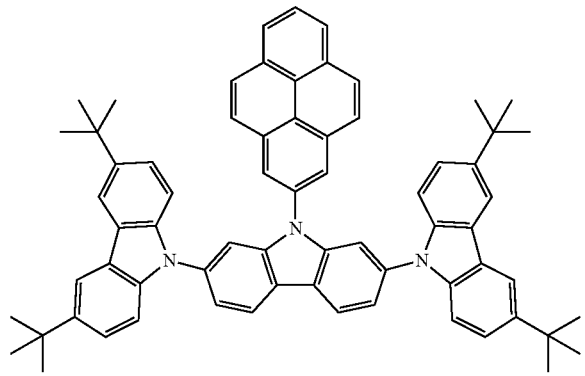

EB-1

<Production of Evaluation Photoelectric Conversion Element>

Example Using Compound (R-1)

The photoelectric conversion element was produced according to the same method as that of the element (A) except that the film thickness of the photoelectric conversion film.

Specifically, the compound (R-1) and the fullerene ($C_{60}$) were subjected to co-vapor deposition by the vacuum evaporation method so as to be respectively 50 nm in terms of single layer on the electron blocking film 16A to form a film in a state where the temperature of the substrate was controlled to 25° C., and the photoelectric conversion film 12 having the bulk hetero structure of 100 nm was formed.

The obtained photoelectric conversion element was to be an element ($B_{R-1}$).

Examples Using Compounds (D-1) to (D-24) or (R-2) to (R-3)

The photoelectric conversion element was produced according to the same method as that of the element ($B_{R-1}$) except that the compound (R-1) was changed to compounds (D-1) to (D-24) or (R-2) to (R-3).

The photoelectric conversion elements obtained using the compounds (D-1) to (D-24) were referred to as elements ($B_{D-1}$) to ($B_{D-24}$), respectively.

On the other hand, in a case where the compounds (R-2) to (R-3) were used, the compounds (R-2) to (R-3) could not be vapor-deposited.

<Evaluation of Photoelectric Conversion Efficiency>

A voltage was applied to each of the produced elements (A), ($B_{D-1}$) to ($B_{D-24}$), and ($B_{R-1}$) so as to obtain an electric field strength of $2.0 \times 10^5$ V/cm, and the maximum value of photoelectric conversion efficiency was measured.

The maximum value of the photoelectric conversion efficiency of the element (A) was set as 1 to evaluate the maximum value of the photoelectric conversion efficiency of each of other elements with respect to that of the element (A) using a relative value. Regarding the relative value of the photoelectric conversion efficiency of the element, a case of 1.1 or more was set as "A", a case of 1.0 or more and less than 1.1 was set as "B", and a case of less than 1.0 was set as "C".

The results are shown in Table 1. For practical use, "A" or "B" is preferable, and "A" is more preferable.

The evaluation results of the elements produced using each compound are shown in Table 1.

In Table 1, the column "$X^1$" indicates whether the group represented by $X^1$ is an oxygen atom or a sulfur atom in a case where the compounds (D-1) to (D-24) were applied to Formula (2). A case where the group represented by $X^1$ is an oxygen atom or a sulfur atom is "presence", and a case where the group is not an oxygen atom or a sulfur atom is "absence".

In Table 1, the column "$R^{b1}$" indicates whether the group represented by $R^{b1}$ is an alkyl group or an aryl group in a case where the compounds (D-1) to (D-24) were applied to Formula (2). A case where the group represented by $R^{b1}$ is an alkyl group or an aryl group is "presence", and a case where the group is not an alkyl group or an aryl group is "absence".

In Table 1, the column "Formula (A2)" indicates the presence or absence of the group represented by Formula (A2) in a case where the compounds (D-1) to (D-24) were applied to Formula (2).

In Table 1, the column "$R^{c3}$" indicates whether the group represented by $R^{c3}$ is an aryl group or a heteroaryl group in a case where the compounds (D-1) to (D-24) were applied to Formula (3). A case where the group represented by $R^{c3}$ is an aryl group or a heteroaryl group is "presence", and a case where the group is not an aryl group or a heteroaryl group is "absence". The compounds which were not applied to Formula (3) was set as "-".

TABLE 1

| | Compound | $X^1$ | $R^{b1}$ | Formula (A2) | $R^{c3}$ | Element | Photoelectric conversion efficiency |
|---|---|---|---|---|---|---|---|
| Example 1 | D-1 | Presence | Presence | Presence | Presence | $B_{D-1}$ | A |
| Example 2 | D-2 | Presence | Presence | Presence | Presence | $B_{D-2}$ | A |
| Example 3 | D-3 | Presence | Presence | Presence | Presence | $B_{D-3}$ | A |
| Example 4 | D-4 | Presence | Presence | Presence | Presence | $B_{D-4}$ | A |
| Example 5 | D-5 | Presence | Presence | Presence | Presence | $B_{D-5}$ | A |
| Example 6 | D-6 | Presence | Presence | Absence | — | $B_{D-6}$ | B |
| Example 7 | D-7 | Presence | Presence | Absence | — | $B_{D-7}$ | B |
| Example 8 | D-8 | Presence | Presence | Absence | — | $B_{D-8}$ | B |
| Example 9 | D-9 | Presence | Presence | Presence | Presence | $B_{D-9}$ | A |
| Example 10 | D-10 | Presence | Presence | Presence | Presence | $B_{D-10}$ | A |
| Example 11 | D-11 | Presence | Presence | Presence | Presence | $B_{D-11}$ | A |
| Example 12 | D-12 | Presence | Presence | Presence | Presence | $B_{D-12}$ | A |
| Example 13 | D-13 | Presence | Presence | Presence | Presence | $B_{D-13}$ | A |
| Example 14 | D-14 | Presence | Presence | Presence | Absence | $B_{D-14}$ | B |
| Example 15 | D-15 | Presence | Presence | Presence | Absence | $B_{D-15}$ | B |
| Example 16 | D-16 | Presence | Presence | Presence | Presence | $B_{D-16}$ | A |

TABLE 1-continued

| | Compound | $X^1$ | $R^{b1}$ | Formula (A2) | $R^{c3}$ | Element | Photoelectric conversion efficiency |
|---|---|---|---|---|---|---|---|
| Example 17 | D-17 | Presence | Presence | Presence | Presence | $B_{D-17}$ | A |
| Example 18 | D-18 | Presence | Presence | Presence | Presence | $B_{D-18}$ | A |
| Example 19 | D-19 | Presence | Presence | Presence | Presence | $B_{D-19}$ | A |
| Example 20 | D-20 | Absence | Presence | Presence | — | $B_{D-20}$ | B |
| Example 21 | D-21 | Presence | Absence | Presence | — | $B_{D-21}$ | B |
| Example 22 | D-22 | Absence | Absence | Absence | — | $B_{D-22}$ | B |
| Example 23 | D-23 | Presence | Presence | Presence | Absence | $B_{D-23}$ | B |
| Example 24 | D-24 | Presence | Presence | Presence | Presence | $B_{D-24}$ | A |
| Comparative Example 1 | R-1 | — | — | — | — | $B_{R-1}$ | C |
| Comparative Example 2 | R-2 | — | — | — | — | Not vapor-deposited | |
| Comparative Example 3 | R-3 | — | — | — | — | Not vapor-deposited | |

As shown in Table 1 above, it was confirmed that the photoelectric conversion element of the embodiment the invention has a photoelectric conversion film excellent in vapor deposition suitability, and exhibits excellent photoelectric conversion efficiency even when the photoelectric conversion film is a thin film.

In a case where $X^1$ in Formula (2) is an oxygen atom or a sulfur atom, it was confirmed that the photoelectric conversion element tends to exhibit more excellent photoelectric conversion efficiency in a case of the thin film (comparison of Example 20 with other examples).

In a case where $R^{b1}$ in Formula (2) is an alkyl group or an aryl group, it was confirmed that the photoelectric conversion element tends to exhibit more excellent photoelectric conversion efficiency in a case of a thin film (comparison of Example 21 with Example 1).

In a case where the compound represented by Formula (2) has a group represented by Formula (A2), it was confirmed that the photoelectric conversion element tens to exhibit more excellent photoelectric conversion efficiency in a case of a thin film (comparison of Examples 6 to 8 with other examples).

In a case where $R^{c3}$ in Formula (3) is an aryl group or a heteroaryl group, it was confirmed that the photoelectric conversion element tends to exhibit more excellent photoelectric conversion efficiency in a case of a thin film (comparison of Examples 14, 15, and 23 with other examples).

<Production of Imaging Element>

The same imaging element as shown in FIG. 3 was produced using the compounds (D-1) to (D-24) and (R-1).

That is, 30 nm of an amorphous TiN was formed into a film on a CMOS substrate by a sputtering method, and was used as the lower electrode through patterning such that each pixel was present on the photodiode (PD) on the CMOS substrate through photolithography, and then the imaging element was produced similarly to the element (A) and the elements ($B_{D-1}$) to ($B_{D-24}$) or (BRA) after the film formation of the electron blocking material. In the obtained imaging element, the photoelectric conversion efficiency in a case where the photoelectric conversion film was a thin film was similarly evaluated, and the same results as in Table 1 were obtained. From this, it was found that the photoelectric conversion element of the embodiment of the invention also exhibits excellent performance in the imaging element.

EXPLANATION OF REFERENCES 10a, 10b: photoelectric conversion element
11: conductive film (lower electrode)
12: photoelectric conversion film
15: transparent conductive film (upper electrode)
16A: electron blocking film
16B: positive hole blocking film
100: pixel separation type imaging element
101: substrate
102: insulating layer
103: connection electrode
104: pixel electrode (lower electrode)
105: connection unit
106: connection unit
107: photoelectric conversion film
108: counter electrode (upper electrode)
109: buffer layer
110: sealing layer
111: color filter (CF)
112: partition wall
113: light shielding layer
114: protective layer
115: counter electrode voltage supply unit
116: readout circuit
200: photoelectric conversion element (hybrid type photoelectric conversion element)
201: inorganic photoelectric conversion film
202: n-type well
203: p-type well
204: n-type well
205: p-type silicon substrate
207: insulating layer
208: pixel electrode
209: organic photoelectric conversion film
210: common electrode
211: protective film
212: electron blocking film

What is claimed is:
1. A photoelectric conversion element comprising:
a conductive film;
a photoelectric conversion film; and
a transparent conductive film, in this order,
wherein the photoelectric conversion film contains a compound represented by Formula (1),

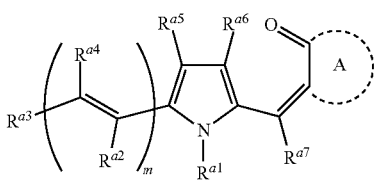

(1)

in Formula (1), m represents an integer of 0 or more,
$R^{a1}$ to $R^{a7}$ each independently represent a hydrogen atom or a substituent,
$R^{a1}$ to $R^{a7}$ may be linked to each other to form a ring,
in a case where a plurality of $R^{a2}$s are present, the plurality of $R^{a2}$s may be linked to each other to form a ring,
in a case where a plurality of $R^{a4}$s are present, the plurality of $R^{a4}$s may be linked to each other to form a ring, and
A represents a ring containing at least two carbon atoms, provided that, the compound represented by Formula (1) does not have any of a carboxy group, a salt of a carboxy group, a phosphoric acid group, a salt of a phosphoric acid group, a sulfonic acid group, or a salt of a sulfonic acid group, and, when m is 1 and $R^{a4}$ and $R^{a5}$ are linked to each other to form a ring, the compound represented by Formula (1) is a compound represented by Formula (2),

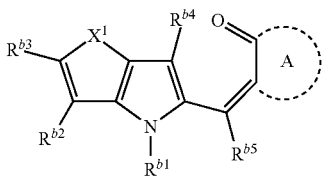

(2)

in Formula (2), $R^{b1}$ to $R^{b5}$ each independently represent a hydrogen atom or a substituent,
$X^1$ represents an oxygen atom, a sulfur atom, a selenium atom, $-NR^{b6}-$, $-CR^{b7}R^{b8}-$, $-SiR^{b9}R^{b10}-$, $-N=CR^{b13}-$, or $-N=N-$,
$R^{b6}$ to $R^{b13}$ each independently represent a hydrogen atom or a substituent,
$R^{b2}$ and $R^{b3}$ may be linked to each other to form a ring, in a case where $X^1$ represents $-NR^{b6}-$, $-CR^{b7}R^{b8}-$, $-SiR^{b9}R^{b10}-$, or $-N=CR^{b13}-$, any one of $R^{b6}$, $R^{b7}$, $R^{b8}$, $R^{b9}$, $R^{b10}$, or $R^{b13}$ included in the group represented by $X^1$ and $R^{b3}$ may be linked to each other to form a ring, and
A represents a ring containing at least two carbon atoms, provided that, the compound represented by Formula (2) does not have any of a carboxy group, a salt of a carboxy group, a phosphoric acid group, a salt of a phosphoric acid group, a sulfonic acid group, or a salt of a sulfonic acid group.

2. The photoelectric conversion element according to claim 1,
wherein the compound represented by Formula (1) is the compound represented by Formula (2).

3. The photoelectric conversion element according to claim 2,
wherein $R^{b1}$ represents an alkyl group, an aryl group, a heteroaryl group, a —CO-alkyl group, a —CO-aryl group, or a —CO-heteroaryl group, which may have a substituent.

4. The photoelectric conversion element according to claim 2,
wherein $X^1$ represents an oxygen atom, a sulfur atom, or $-NR^{b6}-$.

5. The photoelectric conversion element according to claim 2,
wherein $X^1$ represents an oxygen atom or a sulfur atom.

6. The photoelectric conversion element according to claim 1,
wherein the compound represented by Formula (1) is a compound represented by Formula (3),

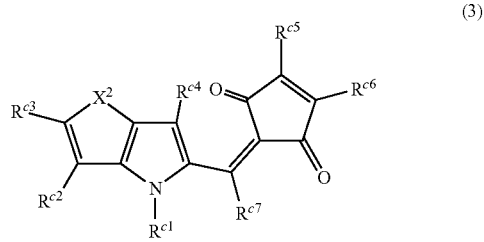

(3)

in Formula (3), $R^{c1}$ represents an alkyl group, an aryl group, a heteroaryl group, a —CO-alkyl group, a —CO-aryl group, or a —CO-heteroaryl group, which may have a substituent,
$R^{c2}$ to $R^{c7}$ each independently represent a hydrogen atom or a substituent,
$X^2$ represents an oxygen atom or a sulfur atom,
$R^{c2}$ and $R^{c3}$ may be linked to each other to form a ring, and
$R^{c5}$ and $R^{c6}$ may be linked to each other to form a ring,
provided that, the compound represented by Formula (3) does not have any of a carboxy group, a salt of a carboxy group, a phosphoric acid group, a salt of a phosphoric acid group, a sulfonic acid group, or a salt of a sulfonic acid group.

7. The photoelectric conversion element according to claim 6,
wherein $R^{c3}$ represents an aryl group or a heteroaryl group, which may have a substituent.

8. The photoelectric conversion element according to claim 1,
wherein the photoelectric conversion film further contains an n-type organic semiconductor and has a bulk hetero structure formed in a state where the compound represented by Formula (1) and the n-type organic semiconductor are mixed.

9. The photoelectric conversion element according to claim 1, further comprising one or more interlayers between the conductive film and the transparent conductive film, in addition to the photoelectric conversion film.

10. An optical sensor comprising the photoelectric conversion element according to claim 1.

11. An imaging element comprising the photoelectric conversion element according to claim 1.

12. A compound represented by Formula (3),

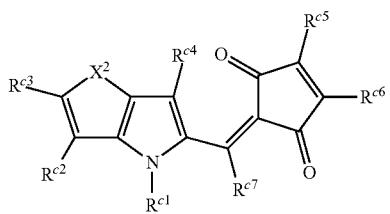

(3)

in Formula (3), $R^{c1}$ represents an alkyl group, an aryl group, a heteroaryl group, a —CO-alkyl group, a —CO-aryl group, or a —CO-heteroaryl group, which may have a substituent, $R^{c2}$ to $R^{c7}$ each independently represent a hydrogen atom or a substituent, $X^2$ represents an oxygen atom or a sulfur atom, $R^{c2}$ and $R^{c3}$ may be linked to each other to form a ring, and $R^{c5}$ and $R^{c6}$ may be linked to each other to form a ring, provided that, the compound represented by Formula (3) does not have any of a carboxy group, a salt of a carboxy group, a phosphoric acid group, a salt of a phosphoric acid group, a sulfonic acid group, or a salt of a sulfonic acid group.

13. The photoelectric conversion element according to claim 3,
wherein $X^1$ represents an oxygen atom, a sulfur atom, or —$NR^{b6}$.

14. The photoelectric conversion element according to claim 3,
wherein $X^1$ represents an oxygen atom or a sulfur atom.

15. The photoelectric conversion element according to claim 2,
wherein the photoelectric conversion film further contains an n-type organic semiconductor and has a bulk hetero structure formed in a state where the compound represented by Formula (1) and the n-type organic semiconductor are mixed.

16. The photoelectric conversion element according to claim 2, further comprising one or more interlayers between the conductive film and the transparent conductive film, in addition to the photoelectric conversion film.

17. An optical sensor comprising the photoelectric conversion element according to claim 2.

18. An imaging element comprising the photoelectric conversion element according to claim 2.

19. The photoelectric conversion element according to claim 4,
wherein $X^1$ represents an oxygen atom or a sulfur atom.

20. The photoelectric conversion element according to claim 3,
wherein the photoelectric conversion film further contains an n-type organic semiconductor and has a bulk hetero structure formed in a state where the compound represented by Formula (1) and the n-type organic semiconductor are mixed.

* * * * *